United States Patent
Müller et al.

(10) Patent No.: US 11,085,038 B2
(45) Date of Patent: Aug. 10, 2021

(54) POLYPEPTIDE LIBRARY

(71) Applicant: MorphoSys AG, Planegg (DE)

(72) Inventors: Roger Müller, Munich (DE); Andreas Bültmann, Planegg (DE); Josef Prassler, Germering (DE); Markus Moosmeier, Landau a.d. Isar (DE)

(73) Assignee: MORPHOSYS AG, Planegg (DE)

( * ) Notice: Subject to any disclaimer, the term of this patent is extended or adjusted under 35 U.S.C. 154(b) by 0 days.

(21) Appl. No.: 16/843,299

(22) Filed: Apr. 8, 2020

(65) Prior Publication Data

US 2020/0231963 A1    Jul. 23, 2020

Related U.S. Application Data

(63) Continuation of application No. 16/080,738, filed as application No. PCT/EP2017/055002 on Mar. 3, 2017, now Pat. No. 10,655,125.

(30) Foreign Application Priority Data

Mar. 4, 2016  (EP) .................................. 16158782

(51) Int. Cl.
  *C40B 40/10*   (2006.01)
  *C12N 15/10*   (2006.01)
  *C40B 40/02*   (2006.01)

(52) U.S. Cl.
  CPC .......... *C12N 15/1037* (2013.01); *C40B 40/02* (2013.01); *C40B 40/10* (2013.01)

(58) Field of Classification Search
  None
  See application file for complete search history.

(56) References Cited

U.S. PATENT DOCUMENTS

| 5,824,483 A | 10/1998 | Houston et al. ................. 506/18 |
| 10,655,125 B2 | 5/2020 | Muller et al. ...... C12N 15/1037 |
| 2003/0170230 A1 | 9/2003 | Caterer et al. ................ 424/130 |

FOREIGN PATENT DOCUMENTS

| WO | WO94/29332 | 12/1994 |
| WO | WO00/27878 | 5/2000 |

OTHER PUBLICATIONS

Bryson et al (Protein Science 7:1404-14) (Year: 1998).*
Fujii, I. "Beyond antibodies: generation of conformationally constrained peptides for molecular-targeting therapy" Yakugaku Zasshi 2009 129:1303-1309.
Fujii et al. "A conformationally purified α-helical peptide library" Tetrahedron Letters 2001 42:3323-3325.
Fujii et al. "Beyond antibodies: directed evolution of molecular-targeting peptides in phage-displayed libraries of conformationally constrained peptides" Drug Delivery System 2011 26:593-603.
Fujiwara & Fujii "Phage selection of peptide "microantibodies"" Current Protocols in Chemical Biology 2013 5:171-194.
Fujiwara et al. "Selection of inhibitory peptides for Aurora-A kinase from a phage-displayed library of helix-loop-helix peptides" Bioorganic and Medicinal Chemistry Letters 2010 20:1776-1778.
Harrison et al. "Downsizing human, bacterial, and viral proteins to short water-stable alpha helices that maintain biological potency" Proc. Natl. Acad. Sci. USA. 2010 107:11686-11691.
Landschultz et al. "The leucine zipper: a hypothetical structure common to a new class of DNA binding proteins" Science 1988 240:1759-1764.
Matsubara et al. "Selection of a carbohydrate-binding domain with a helix-loop-helix structure" Biochemistry 2008 47:6745-6751.
McFarlane et al. "The use of coiled-coil proteins in drug delivery systems" European Journal of Pharmacology 2009 625:101-107.
O'Shea et al. "Evidence that the leucine zipper is a coiled coil" Science 1989 242:538-542.
O'Shea et al. "Preferential heterodimer formation by isolated leucine zippers from fos and jun" Science 1989 245:646-648.
Parry et al. "Fifty years of coiled-coils and α-helical bundles: A Close relationship between sequence and structure" Journal of Structural Biology 2008 163:258-269.
Rudert et al. "A phage-based system to select multiple protein-protein interactions simultaneously from combinatorial libraries" FEBS Letters 1998 440:135-140.
International Search Report and Written Opinion in PCT/EP2017/055002 dated May 17, 2017.
Cohen, C. and Parry, A.D. "α-Helical Coiled Coils and Bundles: How to Design an α-Helical Protein" Proteins: Structure, Function and Genetics 1990 7:1-15.
Eisenberg et al. "Analysis of Membrane and Surface Protein Sequences with the Hydrophobic Moment Plot" J. Mol. Biol. 1984 179:125-142.
Harbury et al. "High Resolution Protein Design with Backbone Freedom" Science 1998 282:1462-1467.
Kohn, W.D. and Hodges, R.S. "De novo design of α-helical coiled coils and bundles: models for the development of protein-design principles" TIBTECH 1998 16:379-389.
Lupas A. and Gruber, M. "The Structure of α-Helical Coiled Coils" Advances in Protein Chemistry 2005 70:37-78.
Mason, J.M. and Arndt, K.M. "Coiled Coil Domains: Stability, Specificity, and Biological Implications" ChemBioChem 2004 5:170-176.
Pace, C.N. and Scholtz. J.M. "A Helix Propensity Scale Based on Experimental Studies of Peptides and Proteins" Biophysical Journal 1998 76:422-427.
Schneider et al. "Analysis and design of three-stranded coiled coils and three-helix bundles" Folding & Design 1998 3:R29-R40.
Woolfson, D.N. "The Design of Coiled-Coil Structures and Assemblies" Advances in Protein Chemistry 2005 70:79-112.

(Continued)

*Primary Examiner* — Christopher M Gross
(74) *Attorney, Agent, or Firm* — Licata & Tyrrell P.C.

(57) ABSTRACT

The invention relates to novel polypeptide libraries that are conformationally constrained in an anti-parallel, helix-turn-helix arrangement. The invention further relates to methods of generating and screening such libraries for biological, pharmaceutical and other uses.

13 Claims, 10 Drawing Sheets

Specification includes a Sequence Listing.

(56) References Cited

OTHER PUBLICATIONS

International Preliminary Examination Report on Patentability in PCT/EP2017/055002 dated Sep. 4, 2018.
Written Opinion in Singapore Application No. 11201806022R dated Aug. 5, 2019.
Pack et al. "Improved Bivalent Miniantibodies, with Identical Avidity as Whole Antibodies, Produced by High Cell Density Fermentation of *Escherichia coli*" Biotechnology 1993 11:1271-1277.
Office Communication dated Oct. 4, 2019 in U.S. Appl. No. 16/080,738, filed Aug. 29, 2018
Office Communication dated Jan. 13, 2020 in U.S. Appl. No. 16/080,738, filed Aug. 29, 2018

* cited by examiner

FIG. 1

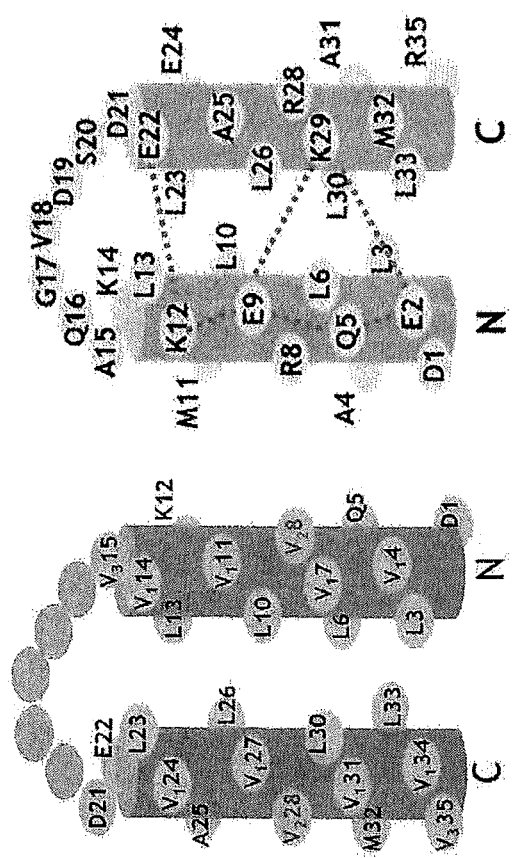
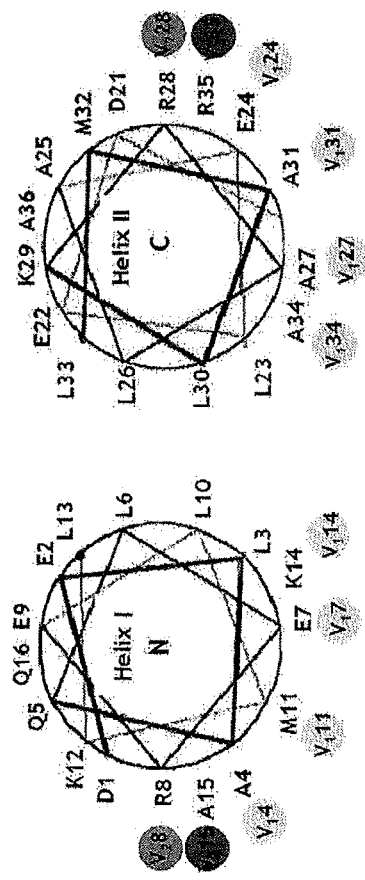
FIG. 2A
FIG. 2B
FIG. 2C

| HTH-lib1 Library | | | | | | | | | | | | | |
|---|---|---|---|---|---|---|---|---|---|---|---|---|---|
| | Helix-1 | | | | | | Helix-2 | | | | | | |
| Position | 4 | 7 | 8 | 11 | 14 | 15 | 24 | 27 | 28 | 31 | 34 | 35 |
| Library Design | Var 1 ADEFHIK LMNQRS TVWY | Var 1 ADEFHIK LMNQRS TVWY | Var 2 EQR | Var 1 ADEFHIK LMNQRS TVWY | Var 1 ADEFHIK LMNQRS TVWY | Var 3 HQR | Var 1 ADEFHIK LMNQRS TVWY | Var 1 ADEFHIK LMNQRS TVWY | Var 2 EQR | Var 1 ADEFHIK LMNQRS TVWY | Var 1 ADEFHIK LMNQRS TVWY | Var 3 HQR |
| A | 10 | 11 | | 4 | 3 | | 14 | 8 | | 5 | 5 | |
| C | | | | | | | | | | | | |
| D | 17 | 7 | | 16 | 12 | | 10 | 9 | | 9 | 9 | |
| E | 13 | 9 | 98 | 9 | 9 | | 10 | 8 | 64 | 11 | 6 | |
| F | 4 | 8 | | 7 | 19 | | 8 | 6 | | 7 | 10 | |
| G | | | | | | | | | | | | |
| H | 11 | 11 | | 10 | 8 | 74 | 2 | 11 | | 17 | 14 | 59 |
| I | 14 | 13 | | 8 | 7 | | 11 | 21 | | 10 | 7 | |
| K | 8 | 10 | | 17 | 10 | | 13 | 7 | | 9 | 7 | |
| L | 4 | 13 | | 10 | 14 | | 11 | 9 | | 5 | 7 | |
| M | 24 | 15 | | 4 | 10 | | 20 | 15 | | 13 | 14 | |
| N | 6 | 8 | | 9 | 7 | | 10 | 7 | | 9 | 9 | |
| P | | | | | | | | | | | | |
| Q | 5 | 10 | 53 | 12 | 13 | 45 | 6 | 9 | 49 | 8 | 11 | 61 |
| R | 9 | 6 | 24 | 21 | 7 | 56 | 18 | 7 | 62 | 18 | 13 | 55 |
| S | 7 | 10 | | 8 | 9 | | 12 | 12 | | 19 | 6 | |
| T | 17 | 11 | | 16 | 10 | | 9 | 12 | | 11 | 15 | |
| V | 7 | 12 | | 6 | 6 | | 7 | 5 | | 9 | 9 | |
| W | 12 | 14 | | 8 | 13 | | 7 | 15 | | 9 | 17 | |
| Y | 7 | 7 | | 10 | 17 | | 7 | 14 | | 6 | 16 | |
| * | | | | | | | | | | | | |
| - | | | | | 1 | | | | | | | |
| Del | | | | | | | | | | | | |
| Ins | | | | | | | | | | | | |
| sum | 175 | 175 | 175 | 175 | 175 | 175 | 175 | 175 | 175 | 175 | 175 | 175 |

FIG. 4B

| HTH-lib1 Library | | Helix-1 | | | | | | Helix-2 | | | | | |
|---|---|---|---|---|---|---|---|---|---|---|---|---|---|
| Position | 4 | 7 | 8 | 11 | 14 | 15 | 24 | 27 | 28 | 31 | 34 | 35 |
| Library Design | Var 1 | Var 1 | Var 2 | Var 1 | Var 1 | Var 3 | Var 1 | Var 1 | Var 2 | Var 1 | Var 1 | Var 3 |
| | ADEFHIK LMNQRS TVWY | ADEFHIK LMNQRS TVWY | EQR | ADEFHIK LMNQRS TVWY | ADEFHIK LMNQRS TVWY | HQR | ADEFHIK LMNQRS TVWY | ADEFHIK LMNQRS TVWY | EQR | ADEFHIK LMNQRS TVWY | ADEFHIK LMNQRS TVWY | HQR |
| Distribution Design: | | | | | | | | | | | | |
| A | 6% | 5% | | 2% | 2% | | 8% | 5% | | 3% | 3% | |
| C | | | | | | | | | | | | |
| D | 10% | 4% | | 9% | 7% | | 6% | 5% | | 5% | 5% | |
| E | 7% | 5% | 56% | 5% | 6% | | 6% | 5% | 37% | 6% | 3% | |
| F | 2% | 5% | 33% | 4% | 11% | | 5% | 3% | 33% | 4% | 6% | |
| G | 6% | 6% | | 6% | 6% | | 6% | 6% | | 6% | 6% | |
| H | 6% | 6% | | 6% | 5% | 42% | 6% | 6% | | 10% | 8% | 34% |
| I | 8% | 7% | | 5% | 4% | | 6% | 12% | | 6% | 4% | |
| K | 6% | 6% | | 10% | 5% | | 7% | 4% | | 5% | 4% | |
| L | 2% | 6% | | 6% | 8% | | 5% | 5% | | 3% | 4% | |
| M | 14% | 9% | | 2% | 6% | | 11% | 9% | | 7% | 8% | |
| N | 3% | 5% | | 5% | 4% | | 6% | 4% | | 5% | 5% | |
| P | | | | | | | | | | | | |
| Q | 3% | 6% | 30% | 7% | 7% | 26% | 3% | 5% | 28% | 5% | 6% | 35% |
| R | 5% | 3% | 14% | 12% | 4% | 32% | 10% | 4% | 35% | 10% | 7% | 31% |
| S | 4% | 5% | 33% | 5% | 5% | 33% | 7% | 7% | 33% | 11% | 3% | 33% |
| T | 10% | 8% | | 9% | 6% | | 5% | 7% | | 6% | 9% | |
| V | 4% | 7% | | 3% | 3% | | 4% | 3% | | 5% | 5% | |
| W | 7% | 8% | | 5% | 7% | | 4% | 9% | | 5% | 10% | |
| Y | 4% | 4% | | 6% | 10% | | 4% | 8% | | 3% | 8% | |
| * | | 6% | | | 6% | | | | | | | |
| Ins | | | | | 1% | | | | | | | |
| Del | | | | | | | | | | | | |

SEQUENCE LISTING

<160> NUMBER OF SEQ ID NOS: 67

<210> SEQ ID NO 1
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

```
<220> FEATURE:
<221> NAME/KEY: VARIANT
<222> LOCATION: (1)..(1)
<223> OTHER INFORMATION: /replace="T" or "N" or "S" or "P"
<220> FEATURE:
<221> NAME/KEY: VARIANT
<222> LOCATION: (2)..(2)
<223> OTHER INFORMATION: /replace="P" or "Q" or "W" or "D"
<220> FEATURE:
<221> NAME/KEY: MOD_RES
<222> LOCATION: (3)..(3)
<223> OTHER INFORMATION: Any amino acid residue having a side chain
      exhibiting a hydrophobicity of greater than 0.62
<220> FEATURE:
<221> NAME/KEY: VARIANT
<222> LOCATION: (4)..(4)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (5)..(5)
<223> OTHER INFORMATION: /replace="A" or "I" or "Q" or "R"
<220> FEATURE:
<221> NAME/KEY: MOD_RES
<222> LOCATION: (6)..(6)
<223> OTHER INFORMATION: Any amino acid residue having a side chain
      exhibiting a hydrophobicity of greater than 0.62
<220> FEATURE:
<221> NAME/KEY: VARIANT
<222> LOCATION: (7)..(7)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (8)..(8)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (9)..(9)
<223> OTHER INFORMATION: /replace="L" or "R" or "M" or "K" or "E"
<220> FEATURE:
<221> NAME/KEY: MOD_RES
<222> LOCATION: (10)..(10)
<223> OTHER INFORMATION: Any amino acid residue having a side chain
      exhibiting a hydrophobicity of greater than 0.62
<220> FEATURE:
<221> NAME/KEY: VARIANT
<222> LOCATION: (11)..(11)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (12)..(12)
<223> OTHER INFORMATION: /replace="L" or "A" or "W" or "F" or "K"
<220> FEATURE:
<221> NAME/KEY: MOD_RES
<222> LOCATION: (13)..(13)
<223> OTHER INFORMATION: Any amino acid residue having a side chain
      exhibiting a hydrophobicity of greater than 0.62
<220> FEATURE:
<221> NAME/KEY: VARIANT
<222> LOCATION: (14)..(14)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (15)..(15)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: MISC_FEATURE
<222> LOCATION: (1)..(15)
```

-continued

<223> OTHER INFORMATION: /note="Variant residues given in the sequence
     have no preference with respect to those in the annotations
     for variant positions"

<400> SEQUENCE: 1

Asp Glu Xaa Ala Met Xaa Ala Ala Xaa Ala Met Xaa Ala Ala
1               5                   10                  15

<210> SEQ ID NO 2
<211> LENGTH: 60
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="T" or "N" or "S" or "P"
<220> FEATURE:
<221> NAME/KEY: VARIANT
<222> LOCATION: (2)..(2)
<223> OTHER INFORMATION: /replace="P" or "Q" or "W" or "D"
<220> FEATURE:
<221> NAME/KEY: MOD_RES
<222> LOCATION: (3)..(3)
<223> OTHER INFORMATION: Any amino acid residue having a side chain
      exhibiting a hydrophobicity of greater than 0.62
<220> FEATURE:
<221> NAME/KEY: VARIANT
<222> LOCATION: (4)..(4)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (5)..(5)
<223> OTHER INFORMATION: /replace="A" or "I" or "Q" or "R"
<220> FEATURE:
<221> NAME/KEY: MOD_RES
<222> LOCATION: (6)..(6)
<223> OTHER INFORMATION: Any amino acid residue having a side chain
      exhibiting a hydrophobicity of greater than 0.62
<220> FEATURE:
<221> NAME/KEY: VARIANT
<222> LOCATION: (7)..(7)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (8)..(8)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (9)..(9)
<223> OTHER INFORMATION: /replace="L" or "R" or "M" or "K" or "E"
<220> FEATURE:
<221> NAME/KEY: MOD_RES
<222> LOCATION: (10)..(10)
<223> OTHER INFORMATION: Any amino acid residue having a side chain
      exhibiting a hydrophobicity of greater than 0.62
<220> FEATURE:
<221> NAME/KEY: VARIANT
<222> LOCATION: (11)..(11)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (12)..(12)
<223> OTHER INFORMATION: /replace="L" or "A" or "W" or "F" or "K"
<220> FEATURE:
<221> NAME/KEY: MOD_RES -continued

```
<222> LOCATION: (13)..(13)
<223> OTHER INFORMATION: Any amino acid residue having a side chain
      exhibiting a hydrophobicity of greater than 0.62
<220> FEATURE:
<221> NAME/KEY: VARIANT
<222> LOCATION: (14)..(14)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (15)..(15)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: MOD_RES
<222> LOCATION: (16)..(45)
<223> OTHER INFORMATION: Any amino acid or not present
<220> FEATURE:
<221> NAME/KEY: MISC_FEATURE
<222> LOCATION: (16)..(45)
<223> OTHER INFORMATION: /note="This region may encompass 1 to 30 amino
      acid residues"
<220> FEATURE:
<221> NAME/KEY: VARIANT
<222> LOCATION: (46)..(46)
<223> OTHER INFORMATION: /replace="T" or "N" or "S" or "P"
<220> FEATURE:
<221> NAME/KEY: VARIANT
<222> LOCATION: (47)..(47)
<223> OTHER INFORMATION: /replace="P" or "Q" or "W" or "D"
<220> FEATURE:
<221> NAME/KEY: MOD_RES
<222> LOCATION: (48)..(48)
<223> OTHER INFORMATION: Any amino acid residue having a side chain
      exhibiting a hydrophobicity of greater than 0.62
<220> FEATURE:
<221> NAME/KEY: VARIANT
<222> LOCATION: (49)..(49)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (50)..(50)
<223> OTHER INFORMATION: /replace="A" or "I" or "Q" or "R"
<220> FEATURE:
<221> NAME/KEY: MOD_RES
<222> LOCATION: (51)..(51)
<223> OTHER INFORMATION: Any amino acid residue having a side chain
      exhibiting a hydrophobicity of greater than 0.62
<220> FEATURE:
<221> NAME/KEY: VARIANT
<222> LOCATION: (52)..(52)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (53)..(53)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (54)..(54)
<223> OTHER INFORMATION: /replace="L" or "R" or "M" or "K" or "E"
<220> FEATURE:
<221> NAME/KEY: MOD_RES
<222> LOCATION: (55)..(55)
<223> OTHER INFORMATION: Any amino acid residue having a side chain
      exhibiting a hydrophobicity of greater than 0.62
<220> FEATURE:
<221> NAME/KEY: VARIANT
<222> LOCATION: (56)..(56)
<223> OTHER INFORMATION: /replace="D" or "E" or "F" or "H" or "I" or "K"
      or "L" or "M" or "N" or "Q" or "R" or "S" or "T" or "V" or "W" or
      "Y"
```

<220> FEATURE:
<221> NAME/KEY: VARIANT
<222> LOCATION: (57)..(57)
<223> OTHER INFORMATION: /replace="L" or "A" or "W" or "F" or "K"
<220> FEATURE:
<221> NAME/KEY: MOD_RES
<222> LOCATION: (58)..(58)
<223> OTHER INFORMATION: Any amino acid residue having a side chain
      exhibiting a hydrophobicity of greater than 0.62
<220> FEATURE:
<221> NAME/KEY: VARIANT
<222> LOCATION: (59)..(59)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (60)..(60)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: MISC_FEATURE
<222> LOCATION: (1)..(60)
<223> OTHER INFORMATION: /note="Variant residues given in the sequence
      have no preference with respect to those in the annotations
      for variant positions"

<400> SEQUENCE: 2

Asp Glu Xaa Ala Met Xaa Ala Ala Ala Xaa Ala Met Xaa Ala Ala Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Asp Glu Xaa
        35                  40                  45

Ala Met Xaa Ala Ala Ala Xaa Ala Met Xaa Ala Ala
    50                  55                  60

<210> SEQ ID NO 3
<211> LENGTH: 60
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (3)..(3)
<223> OTHER INFORMATION: Any amino acid residue having a side chain
      exhibiting a hydrophobicity of greater than 0.62
<220> FEATURE:
<221> NAME/KEY: VARIANT
<222> LOCATION: (4)..(4)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: MOD_RES
<222> LOCATION: (6)..(6)
<223> OTHER INFORMATION: Any amino acid residue having a side chain
      exhibiting a hydrophobicity of greater than 0.62
<220> FEATURE:
<221> NAME/KEY: VARIANT
<222> LOCATION: (7)..(7)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (8)..(8)
<223> OTHER INFORMATION: /replace="D" or "E" or "F" or "H" or "I" or "K"
      or "L" or "M" or "N" or "Q" or "R" or "S" or "T" or "V" or "W" or
      "Y"

```
<220> FEATURE:
<221> NAME/KEY: MOD_RES
<222> LOCATION: (10)..(10)
<223> OTHER INFORMATION: Any amino acid residue having a side chain
      exhibiting a hydrophobicity of greater than 0.62
<220> FEATURE:
<221> NAME/KEY: VARIANT
<222> LOCATION: (11)..(11)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: MOD_RES
<222> LOCATION: (13)..(13)
<223> OTHER INFORMATION: Any amino acid residue having a side chain
      exhibiting a hydrophobicity of greater than 0.62
<220> FEATURE:
<221> NAME/KEY: VARIANT
<222> LOCATION: (14)..(14)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (15)..(15)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: MOD_RES
<222> LOCATION: (16)..(45)
<223> OTHER INFORMATION: Any amino acid or not present
<220> FEATURE:
<221> NAME/KEY: MISC_FEATURE
<222> LOCATION: (16)..(45)
<223> OTHER INFORMATION: /note="This region may encompass 1 to 30 amino
      acid residues"
<220> FEATURE:
<221> NAME/KEY: MOD_RES
<222> LOCATION: (48)..(48)
<223> OTHER INFORMATION: Any amino acid residue having a side chain
      exhibiting a hydrophobicity of greater than 0.62
<220> FEATURE:
<221> NAME/KEY: VARIANT
<222> LOCATION: (49)..(49)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: MOD_RES
<222> LOCATION: (51)..(51)
<223> OTHER INFORMATION: Any amino acid residue having a side chain
      exhibiting a hydrophobicity of greater than 0.62
<220> FEATURE:
<221> NAME/KEY: VARIANT
<222> LOCATION: (52)..(52)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (53)..(53)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: MOD_RES
<222> LOCATION: (55)..(55)
<223> OTHER INFORMATION: Any amino acid residue having a side chain
      exhibiting a hydrophobicity of greater than 0.62
<220> FEATURE:
<221> NAME/KEY: VARIANT
<222> LOCATION: (56)..(56)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: MOD_RES
<222> LOCATION: (58)..(58)
```

-continued

```
<223> OTHER INFORMATION: Any amino acid residue having a side chain
      exhibiting a hydrophobicity of greater than 0.62
<220> FEATURE:
<221> NAME/KEY: VARIANT
<222> LOCATION: (59)..(59)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (60)..(60)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: MISC_FEATURE
<222> LOCATION: (1)..(60)
<223> OTHER INFORMATION: /note="Variant residues given in the sequence
      have no preference with respect to those in the annotations
      for variant positions"

<400> SEQUENCE: 3

Asp Glu Xaa Ala Gln Xaa Ala Ala Glu Xaa Ala Lys Xaa Ala Ala Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Asp Glu Xaa
        35                  40                  45

Ala Ala Xaa Ala Ala Lys Xaa Ala Met Xaa Ala Ala
        50                  55                  60

<210> SEQ ID NO 4
<211> LENGTH: 60
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="T" or "N" or "S" or "P"
<220> FEATURE:
<221> NAME/KEY: VARIANT
<222> LOCATION: (2)..(2)
<223> OTHER INFORMATION: /replace="P" or "Q" or "W" or "D"
<220> FEATURE:
<221> NAME/KEY: VARIANT
<222> LOCATION: (3)..(3)
<223> OTHER INFORMATION: /replace="V" or "I"
<220> FEATURE:
<221> NAME/KEY: VARIANT
<222> LOCATION: (4)..(4)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (5)..(5)
<223> OTHER INFORMATION: /replace="A" or "I" or "Q" or "R"
<220> FEATURE:
<221> NAME/KEY: VARIANT
<222> LOCATION: (6)..(6)
<223> OTHER INFORMATION: /replace="V" or "I"
<220> FEATURE:
<221> NAME/KEY: VARIANT
<222> LOCATION: (7)..(7)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (8)..(8)
```

```
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (9)..(9)
<223> OTHER INFORMATION: /replace="L" or "R" or "M" or "K" or "E"
<220> FEATURE:
<221> NAME/KEY: VARIANT
<222> LOCATION: (10)..(10)
<223> OTHER INFORMATION: /replace="V" or "I"
<220> FEATURE:
<221> NAME/KEY: VARIANT
<222> LOCATION: (11)..(11)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (12)..(12)
<223> OTHER INFORMATION: /replace="L" or "A" or "W" or "F" or "K"
<220> FEATURE:
<221> NAME/KEY: VARIANT
<222> LOCATION: (13)..(13)
<223> OTHER INFORMATION: /replace="V" or "I"
<220> FEATURE:
<221> NAME/KEY: VARIANT
<222> LOCATION: (14)..(14)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (15)..(15)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: MOD_RES
<222> LOCATION: (16)..(45)
<223> OTHER INFORMATION: Any amino acid or not present
<220> FEATURE:
<221> NAME/KEY: MISC_FEATURE
<222> LOCATION: (16)..(45)
<223> OTHER INFORMATION: /note="This region may encompass 1 to 30 amino
      acid residues"
<220> FEATURE:
<221> NAME/KEY: VARIANT
<222> LOCATION: (46)..(46)
<223> OTHER INFORMATION: /replace="T" or "N" or "S" or "P"
<220> FEATURE:
<221> NAME/KEY: VARIANT
<222> LOCATION: (47)..(47)
<223> OTHER INFORMATION: /replace="P" or "Q" or "W" or "D"
<220> FEATURE:
<221> NAME/KEY: VARIANT
<222> LOCATION: (48)..(48)
<223> OTHER INFORMATION: /replace="V" or "I"
<220> FEATURE:
<221> NAME/KEY: VARIANT
<222> LOCATION: (49)..(49)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (50)..(50)
<223> OTHER INFORMATION: /replace="A" or "I" or "Q" or "R"
<220> FEATURE:
<221> NAME/KEY: VARIANT
<222> LOCATION: (51)..(51)
<223> OTHER INFORMATION: /replace="V" or "I"
<220> FEATURE:
<221> NAME/KEY: VARIANT
<222> LOCATION: (52)..(52)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
```

```
<221> NAME/KEY: VARIANT
<222> LOCATION: (53)..(53)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (54)..(54)
<223> OTHER INFORMATION: /replace="L" or "R" or "M" or "K" or "E"
<220> FEATURE:
<221> NAME/KEY: VARIANT
<222> LOCATION: (55)..(55)
<223> OTHER INFORMATION: /replace="V" or "I"
<220> FEATURE:
<221> NAME/KEY: VARIANT
<222> LOCATION: (56)..(56)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (57)..(57)
<223> OTHER INFORMATION: /replace="L" or "A" or "W" or "F" or "K"
<220> FEATURE:
<221> NAME/KEY: VARIANT
<222> LOCATION: (58)..(58)
<223> OTHER INFORMATION: /replace="V" or "I"
<220> FEATURE:
<221> NAME/KEY: VARIANT
<222> LOCATION: (59)..(59)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (60)..(60)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: MISC_FEATURE
<222> LOCATION: (1)..(60)
<223> OTHER INFORMATION: /note="Variant residues given in the sequence
      have no preference with respect to those in the annotations
      for variant positions"

<400> SEQUENCE: 4

Asp Glu Leu Ala Met Leu Ala Ala Ala Leu Ala Met Leu Ala Ala Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Asp Glu Leu
        35                  40                  45

Ala Met Leu Ala Ala Ala Leu Ala Met Leu Ala Ala
    50                  55                  60

<210> SEQ ID NO 5
<211> LENGTH: 60
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="T" or "N" or "S" or "P"
<220> FEATURE:
<221> NAME/KEY: VARIANT
<222> LOCATION: (2)..(2)
<223> OTHER INFORMATION: /replace="P" or "Q" or "W" or "D"
<220> FEATURE:
<221> NAME/KEY: MOD_RES
```

```
<222> LOCATION: (3)..(3)
<223> OTHER INFORMATION: Any amino acid residue having a side chain
      exhibiting a hydrophobicity of greater than 0.62
<220> FEATURE:
<221> NAME/KEY: VARIANT
<222> LOCATION: (4)..(4)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (5)..(5)
<223> OTHER INFORMATION: /replace="A" or "I" or "Q" or "R"
<220> FEATURE:
<221> NAME/KEY: MOD_RES
<222> LOCATION: (6)..(6)
<223> OTHER INFORMATION: Any amino acid residue having a side chain
      exhibiting a hydrophobicity of greater than 0.62
<220> FEATURE:
<221> NAME/KEY: VARIANT
<222> LOCATION: (7)..(7)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (8)..(8)
<223> OTHER INFORMATION: /replace="R" or "Q"
<220> FEATURE:
<221> NAME/KEY: VARIANT
<222> LOCATION: (9)..(9)
<223> OTHER INFORMATION: /replace="L" or "R" or "M" or "K" or "E"
<220> FEATURE:
<221> NAME/KEY: MOD_RES
<222> LOCATION: (10)..(10)
<223> OTHER INFORMATION: Any amino acid residue having a side chain
      exhibiting a hydrophobicity of greater than 0.62
<220> FEATURE:
<221> NAME/KEY: VARIANT
<222> LOCATION: (11)..(11)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (12)..(12)
<223> OTHER INFORMATION: /replace="L" or "A" or "W" or "F" or "K"
<220> FEATURE:
<221> NAME/KEY: MOD_RES
<222> LOCATION: (13)..(13)
<223> OTHER INFORMATION: Any amino acid residue having a side chain
      exhibiting a hydrophobicity of greater than 0.62
<220> FEATURE:
<221> NAME/KEY: VARIANT
<222> LOCATION: (14)..(14)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (15)..(15)
<223> OTHER INFORMATION: /replace="Q" or "H"
<220> FEATURE:
<221> NAME/KEY: MOD_RES
<222> LOCATION: (16)..(45)
<223> OTHER INFORMATION: Any amino acid or not present
<220> FEATURE:
<221> NAME/KEY: MISC_FEATURE
<222> LOCATION: (16)..(45)
<223> OTHER INFORMATION: /note="This region may encompass 1 to 30 amino
      acid residues"
<220> FEATURE:
<221> NAME/KEY: VARIANT
<222> LOCATION: (46)..(46)
<223> OTHER INFORMATION: /replace="T" or "N" or "S" or "P"
<220> FEATURE:
<221> NAME/KEY: VARIANT
<222> LOCATION: (47)..(47)
<223> OTHER INFORMATION: /replace="P" or "Q" or "W" or "D"
```

```
<220> FEATURE:
<221> NAME/KEY: MOD_RES
<222> LOCATION: (48)..(48)
<223> OTHER INFORMATION: Any amino acid residue having a side chain
      exhibiting a hydrophobicity of greater than 0.62
<220> FEATURE:
<221> NAME/KEY: VARIANT
<222> LOCATION: (49)..(49)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (50)..(50)
<223> OTHER INFORMATION: /replace="A" or "I" or "Q" or "R"
<220> FEATURE:
<221> NAME/KEY: MOD_RES
<222> LOCATION: (51)..(51)
<223> OTHER INFORMATION: Any amino acid residue having a side chain
      exhibiting a hydrophobicity of greater than 0.62
<220> FEATURE:
<221> NAME/KEY: VARIANT
<222> LOCATION: (52)..(52)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (53)..(53)
<223> OTHER INFORMATION: /replace="R" or "Q"
<220> FEATURE:
<221> NAME/KEY: VARIANT
<222> LOCATION: (54)..(54)
<223> OTHER INFORMATION: /replace="L" or "R" or "M" or "K" or "E"
<220> FEATURE:
<221> NAME/KEY: MOD_RES
<222> LOCATION: (55)..(55)
<223> OTHER INFORMATION: Any amino acid residue having a side chain
      exhibiting a hydrophobicity of greater than 0.62
<220> FEATURE:
<221> NAME/KEY: VARIANT
<222> LOCATION: (56)..(56)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (57)..(57)
<223> OTHER INFORMATION: /replace="L" or "A" or "W" or "F" or "K"
<220> FEATURE:
<221> NAME/KEY: MOD_RES
<222> LOCATION: (58)..(58)
<223> OTHER INFORMATION: Any amino acid residue having a side chain
      exhibiting a hydrophobicity of greater than 0.62
<220> FEATURE:
<221> NAME/KEY: VARIANT
<222> LOCATION: (59)..(59)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (60)..(60)
<223> OTHER INFORMATION: /replace="Q" or "H"
<220> FEATURE:
<221> NAME/KEY: MISC_FEATURE
<222> LOCATION: (1)..(60)
<223> OTHER INFORMATION: /note="Variant residues given in the sequence
      have no preference with respect to those in the annotations
      for variant positions"

<400> SEQUENCE: 5

Asp Glu Xaa Ala Met Xaa Ala Glu Ala Xaa Ala Met Xaa Ala Arg Xaa
1               5                   10                  15

Xaa Xaa Xaa Xaa Xaa Xaa Xaa Xaa Xaa Xaa Xaa Xaa Xaa Xaa Xaa
            20                  25                  30
```

Xaa Xaa Xaa Xaa Xaa Xaa Xaa Xaa Xaa Xaa Xaa Asp Glu Xaa
            35                  40                  45

Ala Met Xaa Ala Glu Ala Xaa Ala Met Xaa Ala Arg
    50                  55                  60

<210> SEQ ID NO 6
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gln Gly Val Asp Ser
1               5

<210> SEQ ID NO 7
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (4)..(4)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (7)..(7)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (8)..(8)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (11)..(11)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (14)..(14)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (15)..(15)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (24)..(24)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (27)..(27)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:

```
<221> NAME/KEY: VARIANT
<222> LOCATION: (28)..(28)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (31)..(31)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (34)..(34)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: VARIANT
<222> LOCATION: (35)..(35)
<223> OTHER INFORMATION: /replace="D" or "E" or "F" or "H" or "I" or "K"
      or "L" or "M" or "N" or "Q" or "R" or "S" or "T" or "V" or "W" or
      "Y"
<220> FEATURE:
<221> NAME/KEY: MISC_FEATURE
<222> LOCATION: (1)..(35)
<223> OTHER INFORMATION: /note="Variant residues given in the sequence
      have no preference with respect to those in the annotations
      for variant positions"

<400> SEQUENCE: 7

Asp Glu Leu Ala Gln Leu Ala Ala Glu Leu Ala Lys Leu Ala Ala Gln
1               5                   10                  15

Gly Val Asp Ser Asp Glu Leu Ala Ala Leu Ala Ala Lys Leu Ala Met
            20                  25                  30

Leu Ala Ala
        35

<210> SEQ ID NO 8
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Asp Glu Leu Ala Gln Leu Glu Arg Glu Leu Met Lys Leu Lys Ala Gln
1               5                   10                  15

Gly Val Asp Ser Asp Glu Leu Glu Ala Leu Ala Arg Lys Leu Ala Met
            20                  25                  30

Leu Ala Arg
        35

<210> SEQ ID NO 9
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (4)..(4)
<223> OTHER INFORMATION: /replace="R" or "N" or "D" or "E" or "Q" or "H"
      or "I" or "L" or "K" or "M" or "F" or "S" or "T" or "W" or "Y" or
      "V"
<220> FEATURE:
<221> NAME/KEY: VARIANT
```

```
<222> LOCATION: (7)..(7)
<223> OTHER INFORMATION: /replace="R" or "N" or "D" or "E" or "Q" or "H"
      or "I" or "L" or "K" or "M" or "F" or "S" or "T" or "W" or "Y" or
      "V"
<220> FEATURE:
<221> NAME/KEY: VARIANT
<222> LOCATION: (8)..(8)
<223> OTHER INFORMATION: /replace="Q" or "E"
<220> FEATURE:
<221> NAME/KEY: VARIANT
<222> LOCATION: (11)..(11)
<223> OTHER INFORMATION: /replace="R" or "N" or "D" or "E" or "Q" or "H"
      or "I" or "L" or "K" or "M" or "F" or "S" or "T" or "W" or "Y" or
      "V"
<220> FEATURE:
<221> NAME/KEY: VARIANT
<222> LOCATION: (14)..(14)
<223> OTHER INFORMATION: /replace="R" or "N" or "D" or "E" or "Q" or "H"
      or "I" or "L" or "K" or "M" or "F" or "S" or "T" or "W" or "Y" or
      "V"
<220> FEATURE:
<221> NAME/KEY: VARIANT
<222> LOCATION: (15)..(15)
<223> OTHER INFORMATION: /replace="Q" or "H"
<220> FEATURE:
<221> NAME/KEY: VARIANT
<222> LOCATION: (24)..(24)
<223> OTHER INFORMATION: /replace="R" or "N" or "D" or "E" or "Q" or "H"
      or "I" or "L" or "K" or "M" or "F" or "S" or "T" or "W" or "Y" or
      "V"
<220> FEATURE:
<221> NAME/KEY: VARIANT
<222> LOCATION: (27)..(27)
<223> OTHER INFORMATION: /replace="R" or "N" or "D" or "E" or "Q" or "H"
      or "I" or "L" or "K" or "M" or "F" or "S" or "T" or "W" or "Y" or
      "V"
<220> FEATURE:
<221> NAME/KEY: VARIANT
<222> LOCATION: (28)..(28)
<223> OTHER INFORMATION: /replace="Q" or "E"
<220> FEATURE:
<221> NAME/KEY: VARIANT
<222> LOCATION: (31)..(31)
<223> OTHER INFORMATION: /replace="R" or "N" or "D" or "E" or "Q" or "H"
      or "I" or "L" or "K" or "M" or "F" or "S" or "T" or "W" or "Y" or
      "V"
<220> FEATURE:
<221> NAME/KEY: VARIANT
<222> LOCATION: (34)..(34)
<223> OTHER INFORMATION: /replace="R" or "N" or "D" or "E" or "Q" or "H"
      or "I" or "L" or "K" or "M" or "F" or "S" or "T" or "W" or "Y" or
      "V"
<220> FEATURE:
<221> NAME/KEY: VARIANT
<222> LOCATION: (35)..(35)
<223> OTHER INFORMATION: /replace="Q" or "H"
<220> FEATURE:
<221> NAME/KEY: MISC_FEATURE
<222> LOCATION: (1)..(35)
<223> OTHER INFORMATION: /note="Variant residues given in the sequence
      have no preference with respect to those in the annotations
      for variant positions"

<400> SEQUENCE: 9

Asp Glu Leu Ala Gln Leu Ala Arg Glu Leu Ala Lys Leu Ala Arg Gln
1               5                   10                  15

Gly Val Asp Ser Asp Glu Leu Ala Ala Leu Ala Arg Lys Leu Ala Met
                20                  25                  30

Leu Ala Arg
        35

<210> SEQ ID NO 10
<211> LENGTH: 35
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 10

Asp Glu Leu Ala Gln Leu Leu Glu Glu Leu Phe Lys Leu Glu Arg Gln
1               5                   10                  15

Gly Val Asp Ser Asp Glu Leu Ile Ala Leu Trp Arg Lys Leu Ser Met
            20                  25                  30

Leu Trp Gln
        35

<210> SEQ ID NO 11
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Asp Glu Leu Ala Gln Leu Gln Glu Glu Leu Gln Lys Leu His Gln Gln
1               5                   10                  15

Gly Val Asp Ser Asp Glu Leu Leu Ala Leu Asn Arg Lys Leu Arg Met
            20                  25                  30

Leu Gln Arg
        35

<210> SEQ ID NO 12
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Asp Glu Leu Asp Gln Leu Phe Glu Glu Leu Arg Lys Leu Asn Arg Gln
1               5                   10                  15

Gly Val Asp Ser Asp Glu Leu Ser Ala Leu Arg Glu Lys Leu Glu Met
            20                  25                  30

Leu Leu Gln
        35

<210> SEQ ID NO 13
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Asp Glu Leu Asp Gln Leu His Glu Glu Leu Asp Lys Leu Phe Gln Gln
1               5                   10                  15

Gly Val Asp Ser Asp Glu Leu Ser Ala Leu Ser Glu Lys Leu Lys Met
            20                  25                  30

Leu Ser Gln
        35
```

<210> SEQ ID NO 14
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Asp Glu Leu Glu Gln Leu Ala Arg Glu Leu Ala Lys Leu Tyr Arg Gln
1               5                   10                  15

Gly Val Asp Ser Asp Glu Leu Glu Ala Leu Trp Glu Lys Leu Gln Met
            20                  25                  30

Leu Arg Gln
        35

<210> SEQ ID NO 15
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Asp Glu Leu Glu Gln Leu Asp Gln Glu Leu His Lys Leu Tyr Gln Gln
1               5                   10                  15

Gly Val Asp Ser Asp Glu Leu Val Ala Leu Ser Arg Lys Leu Asp Met
            20                  25                  30

Leu Ile Arg
        35

<210> SEQ ID NO 16
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Asp Glu Leu Phe Gln Leu Ala Glu Glu Leu Lys Lys Leu Asp His Gln
1               5                   10                  15

Gly Val Asp Ser Asp Glu Leu Ile Ala Leu Arg Gln Lys Leu Arg Met
            20                  25                  30

Leu Phe His
        35

<210> SEQ ID NO 17
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Asp Glu Leu Phe Gln Leu Thr Gln Glu Leu Ala Lys Leu Tyr His Gln
1               5                   10                  15

Gly Val Asp Ser Asp Glu Leu Asp Ala Leu His Glu Lys Leu Glu Met

-continued

```
                    20                  25                  30

Leu Asn Gln
        35

<210> SEQ ID NO 18
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Asp Glu Leu His Gln Leu Glu Glu Leu Glu Lys Leu Ser Gln Gln
1               5                   10                  15

Gly Val Asp Ser Asp Glu Leu Ile Ala Leu Ile Arg Lys Leu Ile Met
                    20                  25                  30

Leu Met Arg
        35

<210> SEQ ID NO 19
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Asp Glu Leu His Gln Leu His Glu Glu Leu Ile Lys Leu Ile His Gln
1               5                   10                  15

Gly Val Asp Ser Asp Glu Leu Asn Ala Leu Trp Arg Lys Leu Glu Met
                    20                  25                  30

Leu His His
        35

<210> SEQ ID NO 20
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Asp Glu Leu Ile Gln Leu Ala Glu Glu Leu Thr Lys Leu His His Gln
1               5                   10                  15

Gly Val Asp Ser Asp Glu Leu Ala Ala Leu Met Glu Lys Leu Lys Met
                    20                  25                  30

Leu Arg Gln
        35

<210> SEQ ID NO 21
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21
```

Asp Glu Leu Ile Gln Leu Phe Gln Glu Leu Phe Lys Leu Ser His Gln
1               5                   10                  15

Gly Val Asp Ser Asp Glu Leu Thr Ala Leu Lys Arg Lys Leu Phe Met
            20                  25                  30

Leu Lys His
        35

<210> SEQ ID NO 22
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Asp Glu Leu Lys Gln Leu Asn Glu Leu Glu Lys Leu Val Gln Gln
1               5                   10                  15

Gly Val Asp Ser Asp Glu Leu Gln Ala Leu Asp Arg Lys Leu Ala Met
            20                  25                  30

Leu Asn Gln
        35

<210> SEQ ID NO 23
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Asp Glu Leu Lys Gln Leu Tyr Gln Glu Leu Val Lys Leu His His Gln
1               5                   10                  15

Gly Val Asp Ser Asp Glu Leu Ala Ala Leu Trp Arg Lys Leu Asn Met
            20                  25                  30

Leu Tyr Arg
        35

<210> SEQ ID NO 24
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Asp Glu Leu Leu Gln Leu Asp Glu Glu Leu Ser Lys Leu Met Arg Gln
1               5                   10                  15

Gly Val Asp Ser Asp Glu Leu Asp Ala Leu Gln Glu Lys Leu Thr Met
            20                  25                  30

Leu Glu His
        35

<210> SEQ ID NO 25
<211> LENGTH: 35
<212> TYPE: PRT
<213> ORGANISM: Artificial Sequence
<220> FEATURE:

<221> NAME/KEY: source
<223> OTHER INFORMATION: /note="Description of Artificial Sequence: Synthetic polypeptide"

<400> SEQUENCE: 25

Asp Glu Leu Leu Gln Leu Ile Glu Glu Leu Thr Lys Leu Arg His Gln
1               5                   10                  15

Gly Val Asp Ser Asp Glu Leu Met Ala Leu Ala Arg Lys Leu His Met
            20                  25                  30

Leu Thr Gln
        35

<210> SEQ ID NO 26
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 26

Asp Glu Leu Met Gln Leu Asp Glu Glu Leu Lys Lys Leu Thr His Gln
1               5                   10                  15

Gly Val Asp Ser Asp Glu Leu Leu Ala Leu His Glu Lys Leu Ser Met
            20                  25                  30

Leu Tyr His
        35

<210> SEQ ID NO 27
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 27

Asp Glu Leu Met Gln Leu His Gln Glu Leu Lys Lys Leu Gln His Gln
1               5                   10                  15

Gly Val Asp Ser Asp Glu Leu Phe Ala Leu Leu Glu Lys Leu Met Met
            20                  25                  30

Leu Trp Arg
        35

<210> SEQ ID NO 28
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 28

Asp Glu Leu Asn Gln Leu Ala Glu Glu Leu Lys Lys Leu Thr Gln Gln
1               5                   10                  15

Gly Val Asp Ser Asp Glu Leu Met Ala Leu Gln Glu Lys Leu Asn Met
            20                  25                  30

Leu Phe Gln
        35

-continued

```
<210> SEQ ID NO 29
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Asp Glu Leu Gln Gln Leu Lys Gln Glu Leu Arg Lys Leu Lys Gln Gln
1               5                   10                  15

Gly Val Asp Ser Asp Glu Leu Thr Ala Leu Glu Arg Lys Leu Ile Met
            20                  25                  30

Leu Thr Arg
        35

<210> SEQ ID NO 30
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Asp Glu Leu Gln Gln Leu Leu Glu Glu Leu Asp Lys Leu Met Gln Gln
1               5                   10                  15

Gly Val Asp Ser Asp Glu Leu Glu Ala Leu Gln Gln Lys Leu Glu Met
            20                  25                  30

Leu Trp Gln
        35

<210> SEQ ID NO 31
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Asp Glu Leu Arg Gln Leu Ala Glu Glu Leu Val Lys Leu Glu Gln Gln
1               5                   10                  15

Gly Val Asp Ser Asp Glu Leu Gln Ala Leu Arg Gln Lys Leu Leu Met
            20                  25                  30

Leu Thr Gln
        35

<210> SEQ ID NO 32
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Asp Glu Leu Arg Gln Leu Asp Glu Glu Leu Lys Lys Leu Thr His Gln
1               5                   10                  15

Gly Val Asp Ser Asp Glu Leu Arg Ala Leu Tyr Glu Lys Leu Asp Met
            20                  25                  30
```

```
<210> SEQ ID NO 33
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Asp Glu Leu Ser Gln Leu Asp Glu Glu Leu Gln Lys Leu Ser Arg Gln
1               5                   10                  15

Gly Val Asp Ser Asp Glu Leu Glu Ala Leu Met Glu Lys Leu Ser Met
            20                  25                  30

Leu Met His
        35

<210> SEQ ID NO 34
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Asp Glu Leu Ser Gln Leu Glu Glu Glu Leu Phe Lys Leu His Arg Gln
1               5                   10                  15

Gly Val Asp Ser Asp Glu Leu Asp Ala Leu Glu Glu Lys Leu Ile Met
            20                  25                  30

Leu Val His
        35

<210> SEQ ID NO 35
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Asp Glu Leu Thr Gln Leu Ala Glu Glu Leu Ser Lys Leu Glu Gln Gln
1               5                   10                  15

Gly Val Asp Ser Asp Glu Leu Ile Ala Leu Ile Arg Lys Leu His Met
            20                  25                  30

Leu Thr Gln
        35

<210> SEQ ID NO 36
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36
```

```
Asp Glu Leu Thr Gln Leu Lys Glu Glu Leu Lys Lys Leu Leu His Gln
1               5                   10                  15

Gly Val Asp Ser Asp Glu Leu Trp Ala Leu Leu Glu Lys Leu Arg Met
            20                  25                  30

Leu Met Gln
        35
```

<210> SEQ ID NO 37
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

```
Asp Glu Leu Val Gln Leu Asn Glu Glu Leu Lys Lys Leu Phe His Gln
1               5                   10                  15

Gly Val Asp Ser Asp Glu Leu Met Ala Leu Ile Glu Lys Leu Lys Met
            20                  25                  30

Leu Arg Gln
        35
```

<210> SEQ ID NO 38
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

```
Asp Glu Leu Trp Gln Leu Ala Glu Glu Leu Arg Lys Leu Met Arg Gln
1               5                   10                  15

Gly Val Asp Ser Asp Glu Leu Met Ala Leu Trp Gln Lys Leu Val Met
            20                  25                  30

Leu Met Gln
        35
```

<210> SEQ ID NO 39
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

```
Asp Glu Leu Trp Gln Leu His Glu Glu Leu Asp Lys Leu Lys Arg Gln
1               5                   10                  15

Gly Val Asp Ser Asp Glu Leu Gln Ala Leu Val Glu Lys Leu Lys Met
            20                  25                  30

Leu Met His
        35
```

<210> SEQ ID NO 40
<211> LENGTH: 35
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic polypeptide"

<400> SEQUENCE: 40

Asp Glu Leu Tyr Gln Leu Glu Gln Glu Leu Asn Lys Leu Phe His Gln
1               5                   10                  15

Gly Val Asp Ser Asp Glu Leu Lys Ala Leu Ile Arg Lys Leu Val Met
            20                  25                  30

Leu Asp His
        35

<210> SEQ ID NO 41
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Asp Glu Leu Tyr Gln Leu Phe Gln Glu Leu Leu Lys Leu Leu His Gln
1               5                   10                  15

Gly Val Asp Ser Asp Glu Leu Asn Ala Leu Glu Gln Lys Leu Trp Met
            20                  25                  30

Leu Val Arg
        35

<210> SEQ ID NO 42
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 42

His His His His His His
1               5

<210> SEQ ID NO 43
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Asp Glu Leu Met Gln Leu Met Glu Glu Leu Val Lys Leu Asn Gln Gln
1               5                   10                  15

Gly Val Asp Ser Asp Glu Leu Trp Ala Leu His Gln Lys Leu Leu Met
            20                  25                  30

Leu Ser His
        35

<210> SEQ ID NO 44
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 44

Asp Glu Leu Ser Gln Leu Met Glu Glu Leu Glu Lys Leu Asn Arg Gln
1               5                   10                  15

Gly Val Asp Ser Asp Glu Leu Trp Ala Leu His Gln Lys Leu Leu Met
            20                  25                  30

Leu Thr His
        35

<210> SEQ ID NO 45
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Asp Glu Leu Ser Gln Leu Met Gln Glu Leu Thr Lys Leu Asn Gln Gln
1               5                   10                  15

Gly Val Asp Ser Asp Glu Leu Tyr Ala Leu His Gln Lys Leu Leu Met
            20                  25                  30

Leu Thr His
        35

<210> SEQ ID NO 46
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Asp Glu Leu His Gln Leu Ala Glu Glu Leu Trp Lys Leu Asn Gln Gln
1               5                   10                  15

Gly Val Asp Ser Asp Glu Leu Glu Ala Leu His Gln Lys Leu Leu Met
            20                  25                  30

Leu Thr His
        35

<210> SEQ ID NO 47
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Asp Glu Leu Ala Gln Leu Ala Glu Glu Leu Arg Lys Leu Asn Gln Gln
1               5                   10                  15

Gly Val Asp Ser Asp Glu Leu Trp Ala Leu His Gln Lys Leu Leu Met
            20                  25                  30

Leu Ser His
        35

<210> SEQ ID NO 48
<211> LENGTH: 35

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Asp Glu Leu Phe Gln Leu Ala Glu Glu Leu Lys Lys Leu Asn Gln Gln
1               5                   10                  15

Gly Val Asp Ser Asp Glu Leu Ala Ala Leu His Gln Lys Leu Leu Met
            20                  25                  30

Leu Thr His
        35

<210> SEQ ID NO 49
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Asp Glu Leu Leu Gln Leu Ala Glu Glu Leu Asp Lys Leu Asn Arg Gln
1               5                   10                  15

Gly Val Asp Ser Asp Glu Leu Phe Ala Leu His Gln Lys Leu Leu Met
            20                  25                  30

Leu Thr His
        35

<210> SEQ ID NO 50
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Asp Glu Leu Thr Gln Leu Ala Glu Glu Leu Val Lys Leu Asn Gln Gln
1               5                   10                  15

Gly Val Asp Ser Asp Glu Leu Phe Ala Leu His Gln Lys Leu Leu Met
            20                  25                  30

Leu Thr His
        35

<210> SEQ ID NO 51
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Asp Glu Leu Tyr Gln Leu Ile Glu Glu Leu Glu Lys Leu Asn Arg Gln
1               5                   10                  15

Gly Val Asp Ser Asp Glu Leu Ala Ala Leu His Gln Lys Leu Leu Met
            20                  25                  30

Leu Thr His
```

<210> SEQ ID NO 52
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Asp Glu Leu Asp Gln Leu Ile Glu Glu Leu Thr Lys Leu Asn Arg Gln
1               5                   10                  15

Gly Val Asp Ser Asp Glu Leu Phe Ala Leu His Gln Lys Leu Leu Met
            20                  25                  30

Leu Ser His
        35

<210> SEQ ID NO 53
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Asp Glu Leu Leu Gln Leu Ser Glu Glu Leu Tyr Lys Leu Asn Arg Gln
1               5                   10                  15

Gly Val Asp Ser Asp Glu Leu Trp Ala Leu His Gln Lys Leu Leu Met
            20                  25                  30

Leu Ser His
        35

<210> SEQ ID NO 54
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Asp Glu Leu Asn Gln Leu Met Glu Glu Leu Val Lys Leu Asn Gln Gln
1               5                   10                  15

Gly Val Asp Ser Asp Glu Leu Trp Ala Leu His Gln Lys Leu Leu Met
            20                  25                  30

Leu Ser His
        35

<210> SEQ ID NO 55
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Asp Glu Leu Arg Gln Leu Met Glu Glu Leu Lys Lys Leu Asn Gln Gln
1               5                   10                  15

-continued

Gly Val Asp Ser Asp Glu Leu Gln Ala Leu His Gln Lys Leu Leu Met
            20                  25                  30

Leu Thr His
        35

<210> SEQ ID NO 56
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Asp Glu Leu Ala Gln Leu Ala Glu Glu Leu Arg Lys Leu Asn Gln Gln
1               5                   10                  15

Gly Val Asp Ser Asp Glu Leu Tyr Ala Leu His Gln Lys Leu Leu Met
            20                  25                  30

Leu Ser His
        35

<210> SEQ ID NO 57
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Asp Glu Leu Ala Gln Leu Ile Glu Glu Leu Tyr Lys Leu Glu Gln Gln
1               5                   10                  15

Gly Val Asp Ser Asp Glu Leu Asp Ala Leu His Gln Lys Leu Ile Met
            20                  25                  30

Leu Tyr Arg
        35

<210> SEQ ID NO 58
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Asp Glu Leu Asp Gln Leu Glu Glu Glu Leu Trp Lys Leu Asn Gln Gln
1               5                   10                  15

Gly Val Asp Ser Asp Glu Leu Glu Ala Leu His Gln Lys Leu Leu Met
            20                  25                  30

Leu Thr His
        35

<210> SEQ ID NO 59
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Asp Glu Leu Leu Gln Leu Ser Glu Glu Leu Tyr Lys Leu Asn Arg Gln
1               5                   10                  15

Gly Val Asp Ser Asp Glu Leu Tyr Ala Leu His Gln Lys Leu Leu Met
            20                  25                  30

Leu Thr His
        35

<210> SEQ ID NO 60
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Asp Glu Leu Met Gln Leu Phe Glu Glu Leu Thr Lys Leu Asn Gln Gln
1               5                   10                  15

Gly Val Asp Ser Asp Glu Leu Tyr Ala Leu His Gln Lys Leu Leu Met
            20                  25                  30

Leu Thr His
        35

<210> SEQ ID NO 61
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Asp Glu Leu Met Gln Leu Met Glu Glu Leu Val Lys Leu Asn Gln Gln
1               5                   10                  15

Gly Val Asp Ser Asp Glu Leu Phe Ala Leu His Gln Lys Leu Leu Met
            20                  25                  30

Leu Thr His
        35

<210> SEQ ID NO 62
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Asp Glu Leu Gln Gln Leu Lys Glu Glu Leu Thr Lys Leu Asn Gln Gln
1               5                   10                  15

Gly Val Asp Ser Asp Glu Leu Tyr Ala Leu His Gln Lys Leu Leu Met
            20                  25                  30

Leu Tyr His
        35

<210> SEQ ID NO 63
<211> LENGTH: 35
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 63

Asp Glu Leu Ser Gln Leu Met Glu Glu Leu Glu Lys Leu Asn Arg Gln
1               5                   10                  15

Gly Val Asp Ser Asp Glu Leu Ala Ala Leu His Gln Lys Leu Leu Met
            20                  25                  30

Leu Thr His
        35

<210> SEQ ID NO 64
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 64

Asp Glu Leu Ser Gln Leu Met Glu Glu Leu Glu Lys Leu Asn Arg Gln
1               5                   10                  15

Gly Val Asp Ser Asp Glu Leu Phe Ala Leu His Gln Lys Leu Leu Met
            20                  25                  30

Leu Ser His
        35

<210> SEQ ID NO 65
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 65

Asp Glu Leu Thr Gln Leu Ala Glu Glu Leu Lys Lys Leu Asn Gln Gln
1               5                   10                  15

Gly Val Asp Ser Asp Glu Leu Ala Ala Leu His Gln Lys Leu Leu Met
            20                  25                  30

Leu Ser His
        35

<210> SEQ ID NO 66
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 66

Asp Glu Leu Val Gln Leu Arg Gln Glu Leu Ala Lys Leu Ile His Gln
1               5                   10                  15

Gly Val Asp Ser Asp Glu Leu Glu Ala Leu Tyr Arg Lys Leu Met Met
            20                  25                  30

Leu Glu Gln
        35

```
<210> SEQ ID NO 67
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Asp Glu Leu Tyr Gln Leu Ile Glu Glu Leu Glu Lys Leu Asn Arg Gln
1               5                   10                  15

Gly Val Asp Ser Asp Glu Leu Ala Ala Leu His Gln Lys Leu Leu Met
            20                  25                  30

Leu Ser His
        35
```

POLYPEPTIDE LIBRARY

This patent application claims the benefit of priority from U.S. application Ser. No. 16/080,738, filed Aug. 29, 2018, which is the U.S. National Stage of International Application No. PCT/EP2017/055002, filed Mar. 3, 2017, which claims the benefit of priority from EP 16158782.9, filed Mar. 4, 2016, teachings of each of which are incorporated by reference in their entirety.

FIELD OF THE INVENTION

The invention relates to novel polypeptide libraries that are conformationally constrained in an anti-parallel, helix-turn-helix arrangement. The invention further relates to methods of generating and screening such libraries for biological, pharmaceutical and other uses.

BACKGROUND OF THE INVENTION

Peptide libraries have emerged as a powerful resource to identify therapeutically relevant molecules. In addition, peptide libraries are also relevant resources for many other purposes and for basic research.

Therapeutically, peptides have certain advantages over small molecules and large biologics, such as antibodies. As compared to small molecules, peptides typically have a larger interaction interface with an antigen, which comprises hydrogen bonds and van der Waals forces. This leads to high affinity binding, a high specificity for the antigen and typically a high potency. As compared to antibodies, peptides are much smaller and therefore typically penetrate tissue more easily. Certain tumors are inaccessible for antibody therapy.

Numerous phage display peptide libraries do exist, including libraries that utilize constrained peptides. Constraint peptides overcome certain disadvantages that are associated with linear peptides, including weak binding affinities due to a higher conformational flexibility, and an increased susceptibility to proteolytic degradation in the human body.

A natural occurring constrained motif of (poly)peptides is the α-helical bundle. α-helices constitute the largest class of protein secondary structures and play a major role in mediating protein-protein interactions. However, short synthetic peptides of 10-30 amino acids in length are usually not thermodynamically stable helices in water and adopt only random structures (Harrison et al., Proc. Natl. Acad. Sci. USA. 2010 Jun. 29; 107(26)).

α-helical bundles can appear in different forms, including two, four, or even multiple bundles. The individual α-helical peptides in such bundle proteins may be orientated in a parallel or anti-parallel arrangement, thus forming coiled-coil structures in which the helical axes are aligned slightly offset from one another.

The α-helical structures that occur in such bundles usually comprise heptad repeats with a profile consisting of a hydrophilic exterior, a hydrophobic interior and a border of polar amino acid residues that form interhelical salt bridging interactions.

Many natural occurring proteins, like keratin, myosin, epidermin, fibrinogen and tropomysin, have a coiled-coil structure formed by two dimerized α-helical peptides. Furthermore, coiled-coil structures are frequently found on DNA binding proteins, where this motif is referred to as a leucine zipper.

Coiled-coil domains are also found in the Jun, Fos (O'Shea et al., Science. 245:646-648 (1989)), C/EBP (Landschultz et al., Science. 240: 1759-1764 (1988)) and for instance in GCN4 binding proteins (O'Shea et al., Science. 242:538-542 (1989)). Naturally occurring α-helical coiled-coil structure are often found in a parallel orientation, which is thought to be a stable conformation.

Approaches have been described to adapt such structures to design specific recognition molecules. WO94/29332 describes polypeptides containing anti-parallel coiled-coils wherein said scaffolds were modified to incorporate helical recognition sequences from naturally-occurring proteins such as DNA binding proteins and cytokines.

U.S. Pat. No. 5,824,483 describes the construction of a de novo designed and chemically synthesized combinatorial library of α-helical peptides. The α-helical peptides were stabilized by intrahelical lactam bridges and optionally by an additional second α-helical peptide thus resulting in a dimeric coiled-coil structure in a parallel or anti-parallel orientation. However, the only enabled peptide library encompassed a single 24 amino acid long α-helical polypeptide chain which is stabilized via two intrahelical lactam bridges and which is diversified at 5 amino acid positions.

Fujii et al. (Tetrahedron Letters 42, 3323-3325 (2001)) describes a more specific approach for a helix-turn-helix based library. The scientific publication discloses a de novo chemically synthesized anti-parallel orientated helix-turn-helix peptide library wherein the amino- and carboxyl-terminal peptides are linked via a glycine based linker. Each of the two helix-turn-helix forming peptides consisted of 14 amino acids and was stabilized by hydrophobic interactions with leucine residues on the two respective helices. In contrast to the library of the present disclosure, only the carboxyl-terminal helix peptide was diversified at 3 solvent exposed positions with a mixture of 5 naturally occurring amino acid residues.

A complementary method for utilizing a peptide library is the display of such libraries on filamentous bacteriophages. This method allows the preparation of libraries as large as $10^{10}$ unique peptide members, many orders of magnitude larger than libraries that may be prepared synthetically.

A phage displayed anti-parallel orientated helix-turn-helix peptide library was described by Fujii and Coworkers in 2008 (Biochemistry, 47, 6745-6751 (2008)). In contrast to the above mentioned library, the carboxyl-terminal helix peptide was randomized at 5 solvent exposed regions yielding in a theoretical library size of $3.2 \times 10^6$. The library was displayed on the major coat protein VIII of filamentous phage with a glycine/serine linker in conjunction with a detectable tag. A particular utilization of the helix-turn-helix peptide library to generate "Microantibodies" has been further described by Fujii et al. in 2011 (Drug Delivery System, 26-6, 2011, p. 593-603), in 2009 (Yakugaku Zasshi, 129 (11), 1303-1309, 2009) and 2013 (Current Protocols in Chemical Biology, vol. 5 (3), 171-194, 2013)

A common structural feature of the two libraries described by Fujii and Coworkers is the predominant usage of alanine at solvent exposed positions of the two α-helical peptides. Stretches of alanine (poly alanine) are known to facilitate formation of α-helical structures but they also may display low solubility in aqueous solutions and thus are prone for aggregation.

More importantly, the libraries described by Fujii and Coworkers are only diversified within the carboxyl-terminal α-helical peptide by diversifying solvent exposed alanine positions. In this scenario, the non-diversified amino-terminal peptide is thought to retain its α-helical structure and to stabilize the helix-turn-helix structure of the molecule. However, randomization of the carboxyl-terminal α-helical peptide as provided by Fujii still resulted in library members with undesired multiple random like conformations which required a particular purification process in order to enrich for correctly folded helix-turn-helix structures (Fujii et al. (Tetrahedron Letters 42, 3323-3325 (2001)).

A major disadvantage of diversifying only one of the two α-helical peptides lies in the fact that the approach significantly limits the achievable library size and significantly narrows down the interaction interphase between the polypeptides of the library and their bound target molecules of interest resulting in reduced specific and affinity.

Based on limitations of the above mentioned approaches, there is still an unmet need to develop improved helix-turn-helix polypeptide libraries of considerable size.

The library of the present disclosure differs in multiple ways from the libraries disclosed by Fujii. The design of the library of the present disclosure is based on a combined approach taking into account statistical, structural and rational factors. This included in a first instance the analysis and use of the most abundant amino acid residues found at given positions in natural occurring α-helical structures. Such amino acids are considered to have favorable biophysical properties including low immunogenicity, resistance against temperature and chemical denaturation, relative insensitiveness for pH alterations, serum stability and resistance against proteolytic degradation by proteases.

Secondly, the variable positions within the helix-turn-helix library of the present disclosure are present on both, the amino- and the carboxyl terminal α-helical peptide and are displayed in the same relative parallel orientation. This two features enable the formation of a wide and flat interaction interface over the whole length of the helix-turn-helix molecule. The enlarged interaction interface is crucial for an optimal protein-protein interaction with a target antigen of interest resulting in improved specificity and affinity, both critical aspect in the development of therapeutic molecules.

Furthermore, in order to prevent a potential destabilization of the helix-turn-helix scaffold caused by the introduction of a large number of variable positions in both α-helical peptides, additional structural consideration for promoting helix formation and stabilizing the helix-turn-helix structure were taken into account to select the most appropriate amino acid residue at each invariant position. These amino acid residues were selected to stabilize the molecular structure by inter- and intrahelical electrostatical interactions and interhelical hydrogen bonding.

In summary, the library of the present disclosure overcomes the limitations of the helix-turn-helix libraries disclosed by Fujii and Coworkers by maximizing the number of diversified positions without compromising the stabilizing α-helical structures leading to a more efficient development of the resulting polypeptides and an increase in safety and efficacy of the respective therapeutics in patients.

SUMMARY OF THE INVENTION

The present disclosure discloses a helix-turn-helix (HTH) polypeptide library, which is characterized by an extraordinary large library size. Polypeptides can be isolated from this library, which bind to target molecules of interest with high affinity, specificity, and functionality.

Preferably, said polypeptide library is a phage display library.

The sequence variations of the library of the present disclosure is present on both α-helical domains of the HTH scaffold. The polypeptides encoded by the library may therefore bind to, for example, a receptor with two or more spatially distinct but related binding sites. The variable positions present on both α-helical domains may further contribute to an enlarged interaction interphase between a particular polypeptide and its target antigen, thus resulting in improved specificity and affinity.

In another aspect of the present disclosure, the diversified amino acid residue positions are located on the solvent exposed regions of the HTH scaffold as described herein.

The library of the present disclosure can be diversified in up to 12 amino acid positions, each with a mixture of up to 17 natural occurring amino acid residues. Therefore, a library size of greater than $1 \times 10^{11}$ can be achieved.

It was also found that the polypeptides isolated from the library have several superior properties over traditional immunoglobulin and non-immunoglobulin binding agents. Such properties include for instance their compact and small size (~6 kDa), low immunogenicity, extreme stability against thermal and chemical denaturation, relatively insensitiveness to changes in pH and to proteolytic degradation.

The library of the present disclosure can be used to identify molecules for therapeutic use, or can be used to characterize such molecules by means, such as, epitope mapping.

In one aspect the present disclosure provides a library of polypeptides, wherein each member of the library comprises a helix-turn-helix scaffold structure of the formula Helix-1-Li-Helix-2, wherein Helix-1 and Helix-2 comprise a first and second α-helical peptide, wherein each of said α-helical peptides comprises the amino acid sequence (SEQ ID NO: 1)
X1-X2-Hy-Var1-X3-Hy-Var1-Var2-X4-Hy-Var1-X5-Hy- Var1-Var3, wherein
X1 is D, T, N, S or P,
X2 is E, P, Q, W or D,
X3 is M, A, I, Q or R,
X4 is A, L, R, M, K or E,
X5 is M, L, A, W, F or K,
Hy is any amino-acid residue having a side chain exhibiting a hydrophobicity of greater than 0.62, and
Var1, Var2 and Var3 are mixtures of the natural occurring amino acids, excluding G, P and C,
Li is a linker, and
said first and second α-helical peptide form an antiparallel, coiled-coil structure.

In yet a further aspect of the present disclosure the linker Li comprises 1 to 30 amino acid residues (SEQ ID NO: 2).

In another embodiment of the present disclosure (SEQ ID NO: 3),
X1 is D,
X2 is E,
X3 is Q in Helix-1 and A in Helix-2,
X4 is E in Helix-1 and K in Helix-2, and
X5 is K in Helix-1 and M in Helix-2.

In an embodiment, the present disclosure provides a library, wherein Hy is L, V or I (SEQ ID NO: 4).

In an embodiment, the present disclosure provides a library (SEQ ID NO: 5), wherein
Var2 is a mixture of E, R and Q, and
Var3 is a mixture of R, Q and H.

In a further embodiment of the present disclosure, the polypeptides of the library are displayed on bacteriophage.

In a further embodiment of the present disclosure, the library comprises at least 1×10$^6$ polypeptide members.

In a further embodiment of the present disclosure, each member of the library is linked to at least one additional moiety.

In an embodiment of the present disclosure, said additional moiety is an antibody or antibody fragment thereof, a toxin, a cytokine, a reporter enzyme, a moiety being capable of binding a metal ion, a tag suitable for detection and/or purification, a homo- or hetero-association domain, a moiety which increases solubility of a protein, or a moiety which comprises an enzymatic cleavage site.

In a further embodiment, the present disclosure provides a collection of nucleic acid molecules encoding the library members of the present disclosure.

In a further embodiment, the present disclosure provides a vector comprising the collection of nucleic acid molecules encoding the library members of the present disclosure. In certain embodiments, said vector is a display vector or an expression vector.

In a further embodiment, the present disclosure provides a host cell comprising the collection of nucleic acid molecules or the vector encoding the library members of the present disclosure.

In a further embodiment, the present disclosure provides a method to isolate a polypeptide specific for an antigen, said method comprising the steps of:
a. contacting the library according to the present disclosure with an antigen;
b. removing those members of the library which do not bind to the antigen; and
c. recovering those members of the library which did bind to the antigen.

In a further embodiment, the present disclosure provides a polypeptide identified by the method(s) of the present disclosure.

In an embodiment, the present disclosure provides a helix-turn-helix scaffold structure linked to an antibody or an antibody fragment, wherein said helix-turn-helix scaffold structure comprises a first and a second α-helical peptide that form an anti-parallel, coiled-coil structure.

DESCRIPTION OF THE DRAWINGS

FIG. 1 shows an illustration of the helix-turn-helix HTH-lib1 library of the present disclosure. FIG. 1 discloses SEQ ID NO: 1, 7, and 1, respectively, in order of appearance.

FIG. 2A shows a helical wheel cross section for the two α-helical peptides of the helix-turn-helix reference sequence (HTHdes2) of the present disclosure. The diversified amino acid positions Var1, Var2, and Var3 within the HTH-lib1 library of the present disclosure are denoted within the outer circles.

FIG. 2B depicts a three dimensional cartoon of the helix-turn-helix HTH-lib1 library of the present disclosure, indicating the positions of the variable amino-acid residues Var1, Var2 and Var3.

FIG. 2C depicts the HTHdes2 reference sequence with intra- and interchain electrostatic interactions as well as interchain hydrogen bonding between distinct amino acid residues.

FIG. 3 shows the design of the polypeptide library HTH-lib1 as disclosed herein (SEQ ID NO: 8 and 9, respectively, in order of appearance).

FIGS. 4A and 4B shows a quality assessment of the polypeptide library of FIG. 3. FIG. 4A shows the amino acid distribution at diversified positions of the HTH-lib1 library of individually sampled clones using Sanger sequencing. FIG. 4B depicts for each diversified amino acid position the expected amino acid distribution in context of the sequencing results of FIG. 4A.

FIG. 6 discloses "Hiss" as SEQ ID NO: 42.

DEFINITIONS

Figure 5:
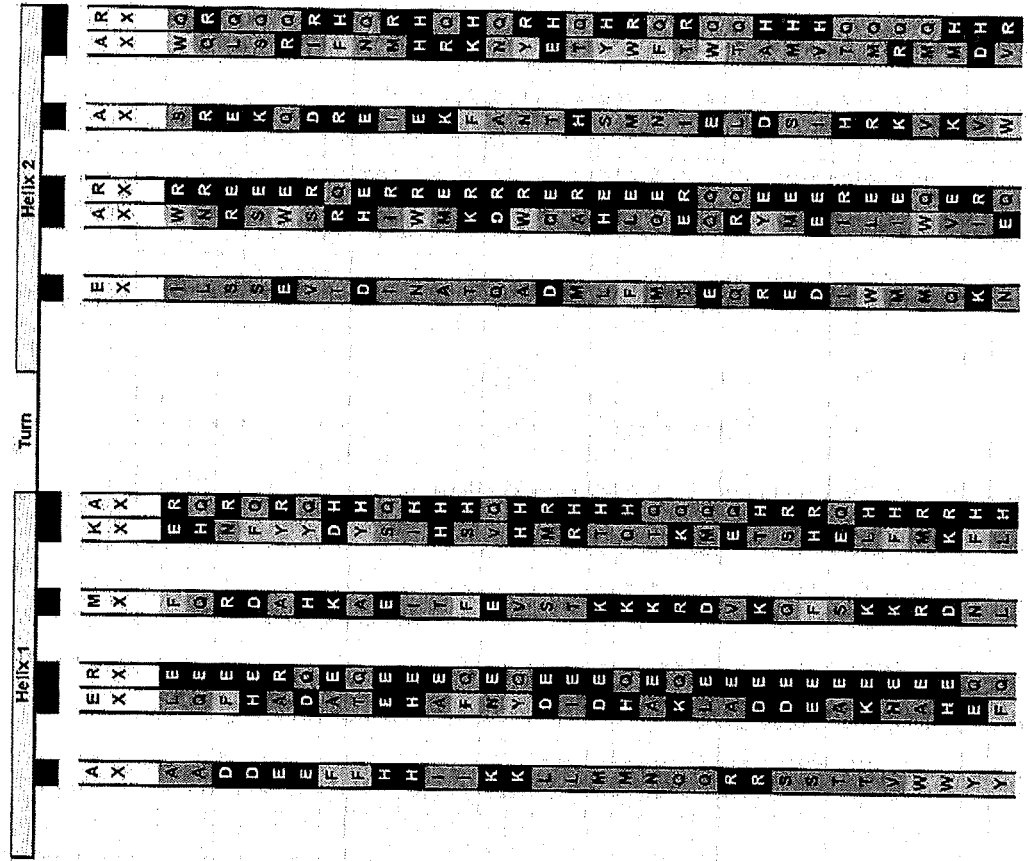
FIG. 5 shows examples of polypeptides from the unselected HTH-lib1 library (SEQ ID NO: 8, 9, and 10 through 41, respectively, in order of appearance). The examples illustrate that the design of the library was successfully produced.
Figure 6:
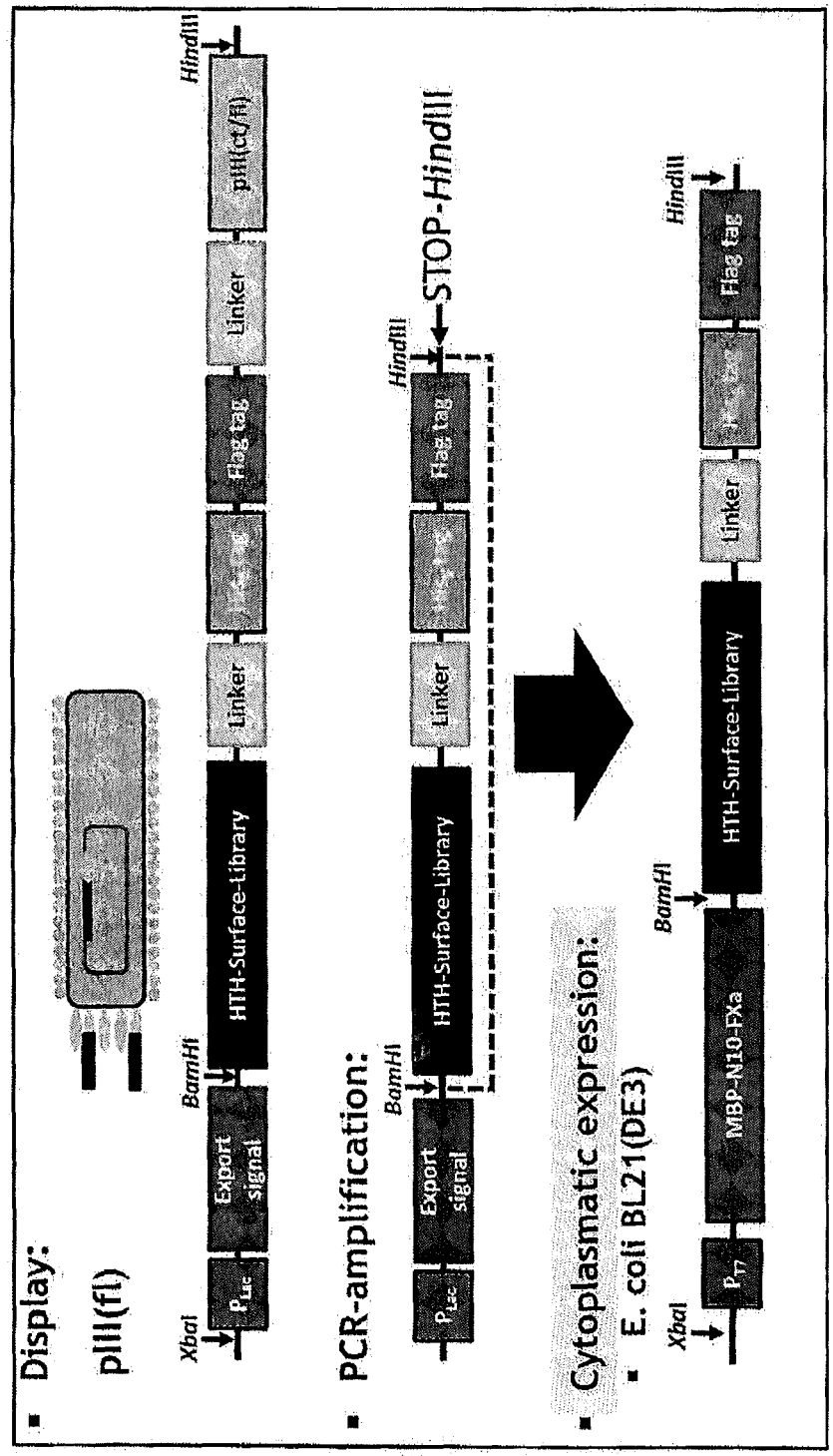
FIG. 6 shows a simplified view of the display and expression vectors as well as the PCR based approach for subcloning a polypeptide-encoding insert from the display vector into the expression vector.
Figure 7:
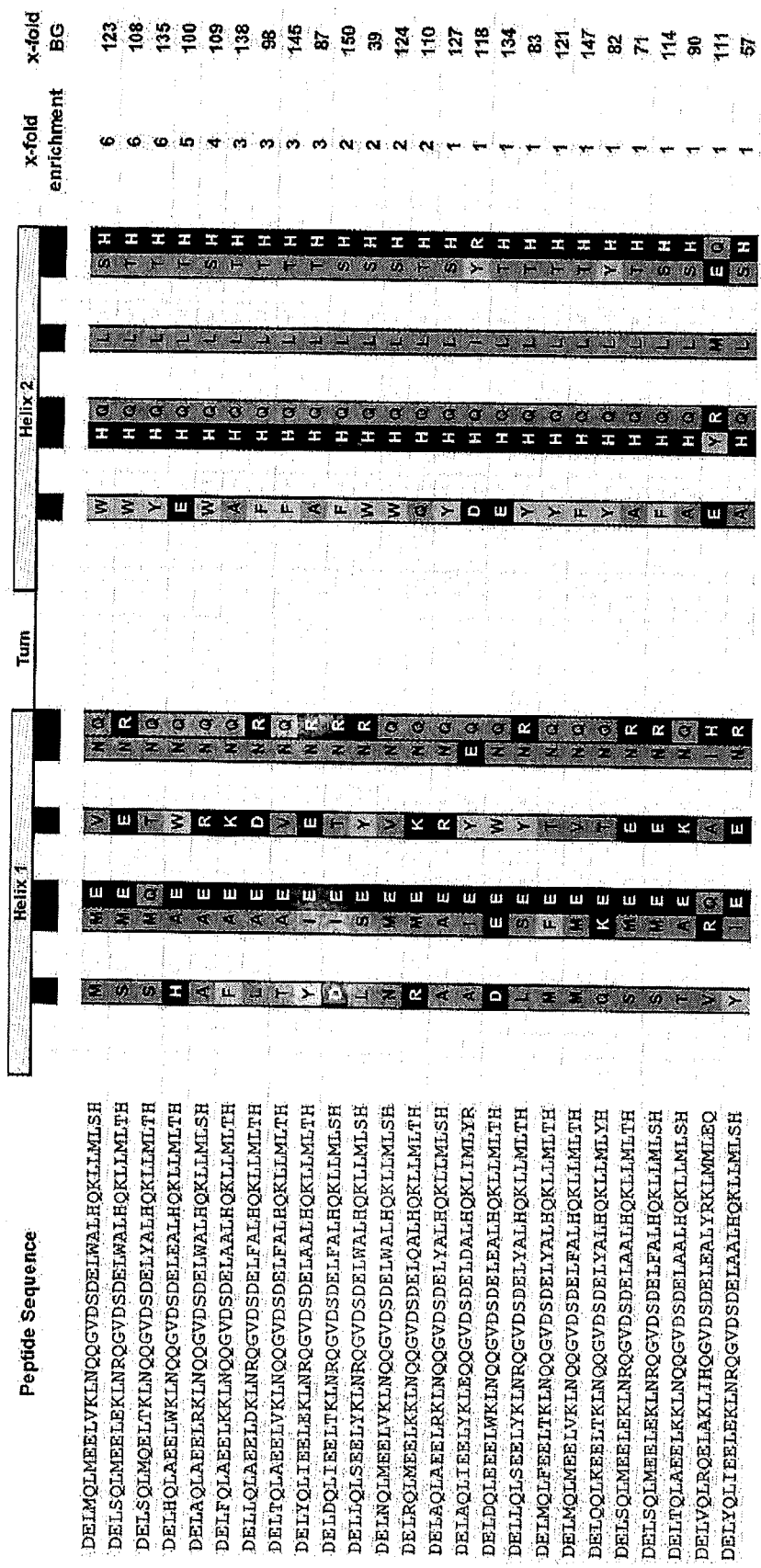
FIG. 7 shows exemplary sequencing results derived from polypeptides identified after an ELISA screening of individual clones derived from a 2$^{nd}$ round panning output of the HTH-lib1 library of FIG. 3 on Target-X. The result confirms that a diverse number of target specific polypeptides can be identified (SEQ ID NO: 43 through 67, respectively, in order of appearance).

The terms "comprising", "comprises" and "comprised of" as used herein are synonymous with "including", "includes" or "containing", "contains", and are inclusive or open-ended and do not exclude additional, non-recited members, elements or method steps.

"Library" means an entity comprising more than one member. In the context of the present disclosure, this term refers to a library of polypeptides, wherein said library comprises at least two different polypeptides.

By the term "peptide" is meant a short molecule having less than or equal to 20 amino acids.

The term "polypeptide" means a molecule having more than 20 amino acids.

A "fusion protein" is a polypeptide having two portions covalently linked together, where each of the portions is a peptide or polypeptide having a different property. The property may be a biological property, such as activity in vitro or in vivo. The property may also be a simple chemical or physical property, such as binding to a target molecule, catalysis of a reaction, etc. The two portions may be linked directly by a single peptide bond or through a peptide spacer containing one or more ammo acid residues. Generally, the two portions and the spacer will be in reading frame with each other.

As used herein, the term "helix-turn-helix scaffold" or "HTH scaffold" refers to a secondary structure of a polypeptide in which two α-helices are orientated in a parallel or an anti-parallel orientation, and in which the two α-helices are linked via a short stretch of amino acids.

The terms "heptad", "heptad unit", "heptad repeat unit" and "heptad motif" are used interchangeably herein and refer to a 7-mer peptide fragment that is repeated two or more times within a HTH scaffold. The tertiary structure of a α-helix is such that 7 amino acid residues in the primary sequence correspond to approximately 2 turns of the α-helix. Accordingly, a primary amino acid sequence giving rise to a α-helical conformation may be broken down into units of 7 residues each. The individual positions of a heptad unit are denoted by small letters, i.e. one heptad unit is for example represented by the sequence 'abcdefg', 'bcdefga', 'cdefgab', 'defgabc', 'efgabcd', 'fgabcde' or 'gabcdef'. The 'a' and the 'd' position of a heptad unit assembled in an HTH scaffold of the present disclosure are of hydrophobic nature. These positions are typically either leucine, isoleucine or valine, and the parallel or the anti-parallel secondary structure of the HTH are formed by hydrophobic interactions via these positions between different heptad units present on two distinct α-helical peptides.

The terms "coiled-coil" and "coiled-coil structure" are used interchangeably herein and will be clear to the person skilled in the art based on the common general knowledge and the description and further references cited herein. In general, a coiled-coil structure is used by nature to stabilize α-helices in proteins. A coiled-coil is a structural motif in polypeptides or proteins in which 2 to 7 α-helices are coiled together. The coiled-coil formation of α-helical peptides is facilitated through a burial of hydrophobic side chains by arranging them on one side of the α-helices so that they are not accessed by polar water molecules. A typical coiled-coil motif (4-3 hydrophobic repeat) is a heptad repeat of amino acids from 'a' to 'g' so that 'a' and 'd' are hydrophobic. Particular reference in this regard is made to review papers concerning coiled-coil structures, such as for example, Cohen and Parry *Proteins* 1990, 7:1-15; Kohn and Hodges *Trends Biotechnol* 1998, 16:379-389; Schneider et al *Fold Des* 1998, 3:R29-R40; Harbury et al. *Science* 1998, 282: 1462-1467; Mason and *Arndt Chem Bio Chem* 2004, 5:170-176; Lupas and Gruber *Adv Protein Chem* 2005, 70:37-78; Woolfson *Adv Protein Chem* 2005, 70:79-112; Parry et al. *J Struct Biol* 2008, 163:258-269; McFarlane et al. *Eur J Pharmacol* 2009, 625:101-107.

As used herein, the term "anti-parallel" refers to an HTH scaffold in which two α-helical peptides of an HTH scaffold are arranged such that the amino-terminal end of one α-helical peptide is aligned with the carboxyl-terminal end of the second α-helical peptide, and vice versa. Thus, the relative orientation of the heptad 'a-g' positions of two interacting α-helices aligned in an anti-parallel orientation is in the opposite direction. For instance, if the heptad positions of a first helix is defined as 'abcdefg' as read from the amino- to the carboxyl-terminus, the heptad positions of a second α-helix in an anti-parallel orientation would be defined as 'gfedcba' as read from the amino- to the carboxyl-terminus.

As used herein, the term "parallel" refers to an HTH scaffold in which the two α-helical peptides are aligned such that they have the same orientation such that the amino-terminal end of one helix is aligned with the amino-terminal end of the second α-helix, and vice versa. Thus, the relative orientation of the heptad 'a-g' positions of two interacting α-helical peptides aligned in parallel orientation is in the same direction. For instance, if the heptad positions of a first helix is defined as 'abcdefg' from the amino-terminus to the carboxyl-terminus, the heptad positions of a second helix in a parallel orientation would be also defined as 'abcdefg' as read from the amino- to the carboxyl-terminus.

The terms "linker", "turn", "linker sequence" or "turn sequence" are used interchangeably herein and refer to an amino acid sequence fragment that is part of the contiguous amino acid sequence of an HTH polypeptide, and covalently links the two α-helical peptide sequences of that polypeptide.

As used herein, the term "single-chain" refers to the HTH scaffold of the present disclosure, wherein the stabilizing coiled-coil structure is formed from different regions of a contiguous amino acid sequence of an HTH polypeptide chain folded back in an appropriate manner.

The term "solvent-oriented" or "solvent-exposed" refers to the region of an entity which is directly exposed or which comes directly into contact with the solvent in the environment or the milieu in which it is present. In the context of the present disclosure it is the α-helix or a α-helical part of an HTH scaffold which is directly exposed or which comes directly into contact with the solvent in the environment or the milieu in which it is present. More particularly, in the context of a binding site, where one or more amino acids located in a solvent-oriented part of the HTH scaffold contribute to the binding site, the binding site is considered to be formed by a solvent-oriented part of the HTH scaffold.

A "α-helical part" of a polypeptide refers to a part of a polypeptide of the present disclosure that has an α-helical secondary structure.

The "hydrophobic core" of an HTH scaffold refers to the part on an HTH scaffold which is not directly exposed to the solvent in which it is present.

As used herein, a polypeptide of the present disclosure "binds specifically to", "specifically binds to", is "specific to/for" or "specifically recognizes" an antigen if such polypeptide is able to discriminate between such antigen and one or more reference antigen(s), since binding specificity is not an absolute, but a relative property. The reference antigen(s) may be one or more closely related antigen(s), which are used as reference points. For example, specific binding can be determined with a standard ELISA assay. Alternative methods comprise, but are not limited to Western blots, ELISA-, RIA-, ECL-, IRMA-tests and peptide scans. The scoring may be carried out by standard color development (e.g. detection antibody with horseradish peroxide and tetramethyl benzidine with hydrogen peroxide). The reaction in certain wells is scored by the optical density, for example, at 450 nm. Typical background (=negative reaction) may be 0.1 OD; typical positive reaction may be 1 OD. This means the difference positive/negative can be more than 10-fold. Typically, determination of binding specificity is performed by using not a single reference antigen, but a set of about three to five unrelated antigens, such as milk powder, BSA, transferrin or the like. Additionally, "specific binding" may relate to the ability to discriminate between different parts of its target antigen, e.g. different domains or regions of said target antigen, or between one or more key amino acid residues or stretches of amino acid residues of a target antigen.

The "affinity" of a polypeptide is represented by the equilibrium constant for the dissociation of the polypeptide and the target protein of interest to which it binds. The lower the $K_D$ value, the stronger the binding strength between the said polypeptide and the target protein of interest to which it binds. Alternatively, the affinity can also be expressed in terms of the affinity constant ($K_A$), which corresponds to $1/K_D$. The binding affinity of a polypeptide can be determined in a manner known to the skilled person, depending on the specific target protein of interest. It is generally known in the art that the $K_D$ can be expressed as the ratio of the dissociation rate constant of a complex, denoted as $k_{Off}$ (expressed in seconds$^{-1}$ or s$^{-1}$), to the rate constant of its association, denoted $k_{On}$ (expressed in molar$^{-1}$ seconds$^{-1}$ or M$^{-1}$ s$^{-1}$). A $K_D$ value greater than about 1 millimolar is considered to indicate non-binding or non-specific binding.

The terms "diversified amino acid residue position" or "variant amino acid residue position" refer to an amino acid residue position at which at least two different amino acid residues may be present.

As used herein, the terms "inhibiting", "reducing" and/or "preventing" refer to a polypeptide according to the present disclosure that specifically binds to a target protein of interest and inhibits, reduces and/or prevents the interaction between that target protein of interest, and its natural binding partner and/or inhibits, reduces and/or prevents a biological activity of that target protein of interest. The inhibiting or antagonizing activity of a polypeptide of the present disclosure may be reversible or irreversible, but for pharmaceutical and pharmacological applications will typically occur reversibly. The inhibiting or antagonizing activity of a polypeptide of the present disclosure may be measured using a suitable in vitro, cellular or in vivo assay.

The term "synthetic" describes a molecule that is made outside of the human body by synthesis or synthesized, e.g. DNA. The term "synthetic" also describes a protein, e.g. antibody or fragment that is translated from a synthetic DNA molecule.

"Linear" as used in the present disclosure refers to a stretch of amino acids or a (poly)-peptide that does not include any secondary or tertiary circular structure.

The term "isolated" refers to a compound which can be e.g. a polypeptide of the disclosure or an antigen binding moiety that is substantially free of other polypeptides or antigen binding moieties having different antigenic specificities. Moreover, an isolated polypeptide or antigen binding moiety may be substantially free of other cellular material and/or chemicals.

"Constrained" as used in the present disclosure refers to a peptide in which the three-dimensional structure is maintained substantially in one spatial arrangement over time. The polypeptides within the present disclosure have a constrained conformation. Methods of determining whether peptides are constrained are known in the art.

"Member" as used in the present disclosure refers to one molecule forming part of a library. In the context of the present disclosure, this term refers to one polypeptide which is part of the polypeptide library.

"Mixture" as used in the present disclosure refers to a solution which contains more than a molecule and in which at least two molecules are different. This term is particularly used in order to describe the amino acid composition at a given position or to describe the codons encoding the respective codons for a given position. For example, each selected codon has a certain probability of occurring at a diversified position. E.g., if Var1 represents an "equal mixture" of the naturally occurring amino acids, then each of the 20 naturally occurring amino acids has the same probability of occurring at that position, i.e. 5%.

As used herein, amino acid residues will be indicated either by their full name or according to the standard three-letter or one-letter amino acid code. "Natural occurring amino acids" means the following amino acids:

TABLE 1

Amino acids

| Amino acid | Three letter code | One letter code |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

"Hydrophobic amino acid residue" refers to an amino acid or residue having a side chain exhibiting a hydrophobicity of greater than zero according to the normalized consensus hydrophobicity scale of Eisenberg et al. (1984, J. Mol. Biol. 179:125-142). Genetically encoded hydrophobic amino acids include P, I, F, V, L, W, M, A and Y.

TABLE 2

Normalized consensus hydrophobicity scale of Eisenberg
Eisenberg consensus scale (ECS)

| R | K | D | Q | N | E | H | S | T | P | Y | C | G | A | M | W | L | V | F | I |
|---|---|---|---|---|---|---|---|---|---|---|---|---|---|---|---|---|---|---|---|
| −2.5 | −1.5 | −0.90 | −0.85 | −0.78 | −0.74 | −0.40 | −0.18 | −0.05 | 0.12 | 0.26 | 0.29 | 0.48 | 0.62 | 0.64 | 0.81 | 1.1 | 1.1 | 1.2 | 1.4 |

The term "vector" refers to a polynucleotide molecule capable of transporting another polynucleotide to which it has been linked. Preferred vectors are those capable of autonomous replication and/or expression of nucleic acids to which they are linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and mammalian vectors). Other vectors can be integrated into the genome of a host cell upon introduction into the host cell, and thereby are replicated along with the host genome. Vectors may be compatible with prokaryotic or eukaryotic cells. Prokaryotic vectors typically include a prokaryotic replicon which may include a prokaryotic promoter capable of directing the expression (transcription and translation) of the peptide in a bacterial host cell, such as *Escherichia coli* transformed therewith. A promoter is an expression control element formed by a DNA sequence that permits binding of RNA polymerase and transcription to occur. Promoter sequences compatible with bacterial hosts are typically provided in plasmid vectors containing convenience restriction sites for insertion of a DNA segment. Examples of such vector plasmids include pUC8, pUC9, pBR322, and pBR329, pPL and pKK223, available commercially.

"Expression vectors" are those vectors capable of directing the expression of nucleic acids to which they are operatively linked and is intended to include such other forms of expression vectors, such as viral vectors (e.g., replication defective retroviruses, adenoviruses and adeno-associated viruses), which serve equivalent functions.

"Display vector" includes a DNA sequence having the ability to direct replication and maintenance of the recombinant DNA molecule extra chromosomally in a host cell, such as a bacterial host cell, transformed therewith. Such DNA sequences are well known in the art. Display vectors can for example be phage vectors or phagemid vectors originating from the class of fd, M13, or fl filamentous bacteriophage. Such vectors are capable of facilitating the display of a protein including, for example, a binding protein or a fragment thereof, on the surface of a filamentous bacteriophage. Display vectors suitable for display on phage, ribosomes, DNA, bacterial cells or eukaryotic cells, for example yeast or mammalian cells are also known in the art, for example, as are viral vectors or vectors encoding chimeric proteins.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Typical host cells are prokaryotic (such as bacterial, including but not limited to *E. coli*) or eukaryotic (which includes yeast, mammalian cells, and more). Bacterial cells are preferred prokaryotic host cells and typically are a strain of *Escherichia coli* (*E. coli*) such as, for example, the *E. coli* strain DH5 available from Bethesda Research Laboratories, Inc., Bethesda, Md. Preferred eukaryotic host cells include yeast and mammalian cells including murine and rodents, preferably vertebrate cells such as those from a mouse, rat, monkey or human cell line, for example HKB11 cells, PERC.6 cells, or CHO cells.

The term "epitope" refers to an antigenic determinant, i.e. the part of an antigen that is recognized by a binding molecule, such as an antibody or a peptide.

The terms "binding region", "binding site" and "interaction site" as used herein refer to a particular site, part, domain or stretch of amino acid residues present on the polypeptides of the present disclosure that is responsible for binding to a target molecule. Such binding region consists of specific amino acid residues from the said polypeptide which are in contact with the target molecule.

"Phage display" is a technique by which variant polypeptides are displayed as fusion proteins to a coat protein on the surface of phage, e g filamentous phage particles, while the genetic material encoding each variant resides on the inside. This creates a physical linkage between each variant protein sequence and the DNA encoding it, which allows rapid partitioning based on binding affinity to a given target molecule (antibodies, enzymes, cell-surface receptors, etc.) by an in vitro selection process called panning. In its simplest form, panning is carried out by incubating a library of phage-displayed peptides on a plate (or bead) coated with the target, washing away the unbound phage, and eluting the specifically bound phage. The eluted phage are then amplified and taken through additional binding/amplification cycles to enrich the pool in favor of binding sequences. After a few rounds, individual clones are characterized by DNA sequencing and ELISA.

A utility of phage display lies in the fact that large libraries of randomized protein variants can be rapidly and efficiently sorted for those sequences that bind to a target molecule with high affinity display of peptides and proteins libraries on phage has been used for screening millions of polypeptides for ones with specific binding properties. Polyvalent phage display methods have been used for displaying small random peptides and small proteins through fusions to either gene III or gene VIII of filamentous phage (Wells and Lowman ((1992) Curr Opin Struct Biol B 355-362) and references cited therein). In monovalent phage display, a protein or peptide library is linked to a gene III or a portion thereof and expressed at low levels in the presence of wild type gene III protein so that phage particles display one copy or none of the fusion proteins.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as, an M13, fd phage or a derivative thereof, a lambdoid phage, such as lambda, a Baculovirus, a T4 phage, a T7 phage virus, or a derivative of any of the foregoing.

The term "coat protein" means a protein, at least a portion of which is present on the surface of the virus particle. From a functional perspective, a coat protein is any protein which associates with a virus particle during the viral assembly process in a host cell, and remains associated with the assembled virus until it infects another host cell. The coat protein may be the major coat protein, such as pVIII, or may be a minor coat protein, such as pIII.

The term "antibody" as used herein refers to a protein comprising at least two heavy (H) chains and two light (L) chains inter-connected by disulfide bonds which interacts with an antigen. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FR's arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. The term "antibody" includes for example, monoclonal antibodies, human antibodies, humanized antibodies, camelised antibodies and chimeric antibodies. The antibodies can be of any isotype (e.g., IgG, IgE, IgM, IgD, IgA and IgY), class (e.g., IgG1, IgG2, IgG3, IgG4, IgA1 and IgA2) or subclass. Both the light and heavy chains are divided into regions of structural and functional homology.

The phrase "antibody fragment", as used herein, refers to one or more portions of an antibody that retain the ability to specifically interact with (e.g., by binding, steric hindrance, stabilizing spatial distribution) an antigen. Examples of binding fragments include, but are not limited to, a Fab fragment, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., (1989) Nature 341:544-546), which consists of a VH domain; and an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., (1988) Science 242:423-426; and Huston et al., (1988) Proc. Natl. Acad. Sci. 85:5879-5883). Such single chain antibodies are also intended to be encompassed within the term "antibody fragment". These antibody fragments are obtained using conventional techniques known to those of skill in the art, and the fragments are screened for utility in the same manner as are intact antibodies. Antibody fragments can also be incorporated into single domain antibodies, maxibodies, minibodies, intrabodies, diabodies, triabodies, tetrabodies, v-NAR and bis-scFv (see, e.g., Hollinger and Hudson, (2005) Nature Biotechnology 23:1126-1136). Antibody fragments can be grafted into scaffolds based on polypeptides such as Fibronectin type III (Fn3) (see U.S. Pat. No. 6,703,199, which describes fibronectin polypeptide monobodies). Antibody fragments can be incorporated into molecules comprising a pair of tandem Fv segments (VH—CH1-VH—CH1) which, together with complementary light chain polypeptides, form a pair of antigen-binding sites (Zapata et al., (1995) Protein Eng. 8:1057-1062; and U.S. Pat. No. 5,641,870).

DETAILED DESCRIPTION OF THE INVENTION

The present disclosure provides novel polypeptide libraries that are conformationally constrained in an anti-parallel, helix-turn-helix (HTH) arrangement. The present disclosure further relates to methods of generating and screening such libraries to identify polypeptides for biological, pharmaceutical and other uses.

The polypeptide library of the present disclosure can be used for the screening and/or selection of one or more polypeptides that specifically bind to a target molecule of interest.

It has been found that polypeptides isolated from the library have certain preferred properties and are superior over other binding agents known in the art. Such properties include target binding with high affinities, a compact and small size (~6 kDa), low immunogenicity, extreme stability against thermal and chemical denaturation, and insensitiveness to changes in pH and to proteolytic degradation.

Design of the Library

In order to design a scaffold structure suitable for a structurally constraint presentation of the various sequence combinations, a novel and unique approach in combining statistical and structural amino acid propensities occurring in natural α-helices was used.

The most abundant amino acid residues found in natural α-helices may have favorable biophysical properties that lead to more efficient development and increase the safety and efficacy of the resulting polypeptides in patients. Such favorable biophysical properties include high relative display rate, high expression yields, low immunogenicity, resistance against temperature and chemical denaturation, relative insensitiveness for pH alterations, serum stability and resistance against proteolytic degradation by proteases.

Data about the abundancy of natural occurring amino acids in α-helices can be obtained from publically available literature, such as Aurora et al. (Protein Science (1998), 7:21-38) and Pace et al. (Biophysical Journal (1998), Vol. 75, 422-427). These data can be compiled to catalog amino acid preferences at certain positions of the α-helical coiled-coil structure in an aqueous solution. By this approach a design template can be generated, e.g. a design template for a α-helical reference sequence consisting of 15 amino acid residues, consisting of two consecutive heptad sequences.

For each of said 15 amino acid residue positions, the five to six most frequently occurring amino acids residues are considered as a basis for designing two independent α-helical peptide sequences, named Helix-1 and Helix-2, respectively.

In order to select the optimal reference sequence for the generation of a polypeptide library according of the present disclosure, additional structural consideration for promoting helix formation and stabilizing the α-helical coiled-coil structure were taken into account to select the most appropriate amino residue at each position.

Accordingly, a reference polypeptide sequence (HTHdes2) comprising two α-helical peptides and a linker segment was designed. Testing via circular dichroism (CD) spectra measurements confirmed that the HTHdes2 reference sequence resulted in a high degree of α-helical content and a low content of random coiled structures in solution. Additional studies revealed that the HTHdes2 sequence is extreme resistant towards thermal and chemical denaturation.

The polypeptide library of the present disclosure is based on a helix-turn-helix (HTH) scaffold structure which comprises two α-helical peptides which are orientated in an anti-parallel arrangement, such that said α-helical peptides are capable of forming a stabilized coiled-coil structure. The two α-helical peptides constituting the HTH scaffold of the present disclosure are herein referred to as Helix-1 and Helix-2.

Accordingly, Helix-1 and Helix-2 assemble into a helix-turn-helix scaffold in an anti-parallel configuration, wherein the two helices are arranged such that the amino-terminal end of Helix-1 is aligned with the carboxyl-terminal end of Helix-2.

In certain embodiments of the disclosure, the two α-helical peptides, Helix-1 and Helix-2, are of similar size, each ranging from about 10 to about 50 residues in length. In another embodiment, Helix-1 and Helix-2 are of equal length. In another embodiment, Helix-1 and Helix-2 are 15 amino acid residues in length.

The assembly of Helix-1 and Helix-2 occurs due to the presence of a repeated heptad motif of conserved amino acid residues.

In a preferred embodiment of the present disclosure, Helix-1 and Helix-2 are formed by a single polypeptide wherein the two α-helical peptides are either directly linked via a single peptide bond to each other, or are linked by a linker segment that does not substantially interfere with the association of Helix-1 and Helix-2 into a coiled-coil structure.

In an embodiment of the present disclosure, the two α-helical peptides are covalently linked by a flexible linker (Li) in a way that the carboxyl-terminus of the first α-helical peptide (Helix-1) is linked to the amino-terminus of the second α-helical peptide (Helix-2).

Thus, according to a specific embodiment of the present disclosure, the HTH scaffold structure of the library of the present disclosure comprises the general formula Helix-1-Li-Helix-2.

Each of the scaffold structure forming α-helical peptides is comprised of a peptide whose sequence contains "invariant" positions, i.e. positions which contain the same amino acid residues in each member of the library, and "variable" positions, i.e. positions which contain different amino acid residues in the different members of the library. These variable positions are important to diversify the library, i.e. to generate a library consisting of different members.

In an embodiment of the present disclosure, the introduced sequence variation or variable positions within the library is present on both α-helical peptides, which form the HTH scaffold of the present disclosure.

In an embodiment of the present disclosure, Helix-1 and Helix-2 may have the same amino acid residues at their invariant positions.

In another embodiment of the present disclosure, Helix-1 and Helix-2 have different amino acid residues at their invariant positions.

In particular embodiments of the present disclosure, the invariant positions of Helix-1 and Helix-2 do not correspond to a naturally occurring protein sequence. In another embodiment of the present disclosure, the invariant positions of Helix-1 and Helix-2 are of non-natural origin. In another embodiment of the present disclosure, the invariant positions of Helix-1 and Helix-2 is are artificial sequences.

Figure 1:
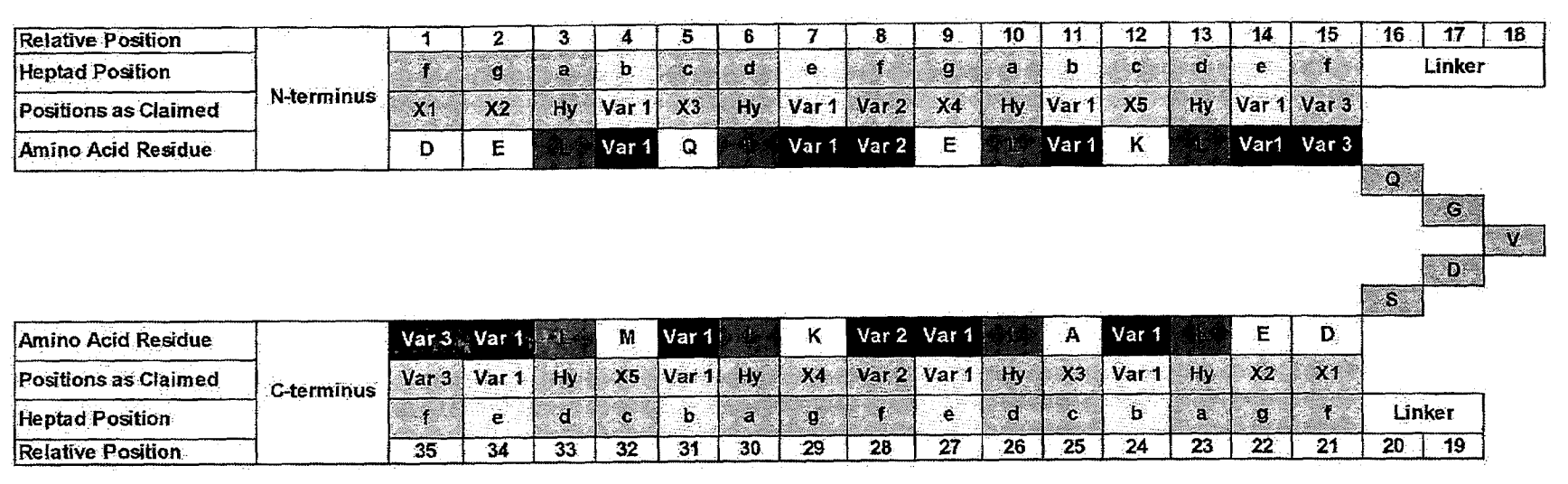

In an aspect of the present disclosure, the amino acid residues present at the invariant positions of Helix-1 and Helix-2 are referred to as X1, X2, X3, X4, X5, and Hy, respectively (see FIG. 1).

The invariant amino acid residues X1, X2, X3, X4, and X5 are solvent exposed since they are located at the outward-facing side of the HTH scaffold, and are in contact with the solvent when the HTH scaffold structure is in solution.

In an embodiment of the present disclosure, the invariant amino acid residue X1 is selected from the group of D, T, N, S and P. In another embodiment of the present disclosure, the invariant amino acid residue X1 is D in Helix-1 and D in Helix-2.

In an embodiment of the present disclosure, the invariant amino acid residue X2 is selected from the group of E, P, Q, W and D. In another embodiment of the present disclosure, the invariant amino acid residue X2 is E in Helix-1 and E in Helix-2.

In an embodiment of the present disclosure, the invariant amino acid residue X3 is selected from the group of M, A, I, Q and R. In another embodiment of the present disclosure, the invariant amino acid residue X3 is Q in Helix-1 and A in Helix-2.

In an embodiment of the present disclosure, the invariant amino acid residue X4 is selected from the group of A, L, R, M, K and E. In another embodiment of the present disclosure, the invariant amino acid residue X4 is E in Helix-1 and K in Helix-2.

In an embodiment of the present disclosure, the invariant amino acid residue X5 is selected from the group of M, L, A, W, F and K. In another embodiment of the present disclosure, the invariant amino acid residue X5 is K in Helix-1 and M in Helix-2.

The amino acid residues that are varied in the polypeptide library of the present disclosure and that contribute to diversity are referred to as Var1 Var2, and Var3. This corresponds to heptad positions b, e, and f of the α-helical peptides Helix-1 and Helix-2.

Helix-1 and Helix-2 reversibly bind to one another in a manner that is determined by the identity of the residues at the invariant positions of the two α-helical peptides Helix-1 and Helix-2.

Helix-1 and Helix-2 of to the present disclosure are each comprised of two "heptads" and thus may be referred to as a "heptad repeats". The heptad repeats give rise to regularly repeating heptad positions, corresponding to regularly-repeating amino acid residues along the α-helix (FIGS. 1 and 3).

Figure 3:
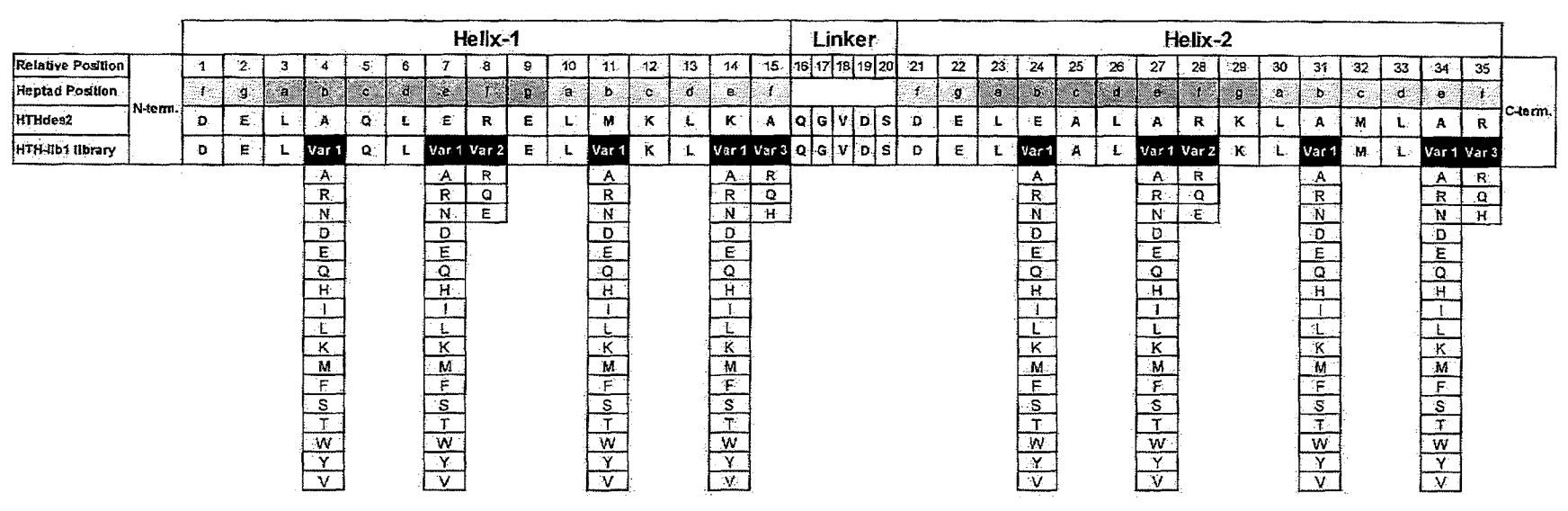

The relative orientations of the 'a-g' positions of the two interacting α-helices arranged in an anti-parallel configuration of the present disclosure is shown in FIGS. 1 and 3.

In an aspect of the present disclosure, the HTH scaffold is stabilized primarily by non-covalent bonds. In preferred embodiments, said non-covalent bonds are formed by hydrophobic interactions between hydrophobic residues at the contact region between Helix-1 and Helix-2.

Accordingly, the individual α-helical peptides Helix-1 and Helix-2 contact one another along their respective hydrophobic faces, formed by the regularly repeating amino acid residues Hy. This corresponds to heptad positions 'a' and 'd'.

The contact region of Helix-1 and Helix-2 comprises the hydrophobic core of the helix-turn-helix scaffold of the present disclosure. In one aspect, said hydrophobic amino acids residues are invariant amino acid residues.

The appropriate selection of the hydrophobic residues Hy at the heptad positions 'a' and 'd' position is important for the formation of a coiled-coil structure.

In an embodiment of the present disclosure, said hydrophobic amino acids have a hydrophobicity of greater 0.62 according to the normalized consensus hydrophobicity scale of Eisenberg et al. (1984, J. Mol. Biol. 179:125-142).

In an embodiment of the present disclosure, Hy is an hydrophobic amino acid selected from the group, such as I, F, V, L, W, M. In another embodiment of the present disclosure, Hy is selected from the group of I, L, and V. In yet another embodiment of the present disclosure, the hydrophobic amino acid Hy is L.

In further embodiments, the HTH scaffold of the present disclosure may be further stabilized by the introduction of negatively charged amino acid residues at the amino-terminal end of each α-helical peptide. This may stabilizes the dipole moment of the α-helices of said peptides. Such a negatively charged amino acid residue can be D or E. In another embodiment, such a negatively charged amino acid residue is D.

In further embodiments, the HTH scaffold of the present disclosure may further be stabilized by inter- or intrahelical electrostatical interactions. Such electrostatical interactions may be ionic interactions.

In further embodiments, the HTH scaffold of the present disclosure is stabilized by intrahelical ionic interactions between the invariant amino acid residues X2 of Helix-1 and X4 of Helix-2,
X4 of Helix-1 and X4 of Helix-2, and/or
X5 of Helix-1 and X2 of Helix 2.

Preferably, X2 and X4 of Helix-1 are negatively charged amino acid residues and X5 is a positively charged amino acid residue. Negatively charged amino acid residue may be D or E, positively charged amino acid residue may be K, H or R.

Preferably, X2 of Helix-2 is a negatively charged amino acid residue and X4 of Helix-2 is a positively charged amino acid residue.

In further embodiments, the HTH scaffold of the present disclosure is stabilized by interhelical ionic interactions between the invariant amino acid residues X4 and X5 of Helix-1. Preferably, X4 is a negatively charged amino acid residue and X5 is a positively charged amino acid residue. In another embodiment, X4 is E and X5 is K.

In further embodiments, the HTH scaffold of the present disclosure is stabilized by interhelical hydrogen bonding.

In one embodiment, said interhelical hydrogen bonding is between the invariant amino acid residues X2 and X3 and/or between X3 and X4 of Helix-1. In another embodiment, X2 is E, X3 is Q and X4 is E.

Linker

The two α-helical peptides (Helix-1 and Helix-2) of the present disclosure are linked via a peptide linker (Li) which connects the carboxyl-terminus of Helix-1 to the amino terminus of Helix-2 thus resulting in a single-chain amino acid sequence for the polypeptides of the disclosure.

In an embodiment, Helix-1, Li and Helix-2 are covalently linked in a way that the carboxyl-terminus of Helix-1 is linked to the amino-terminus of Li and that the carboxyl-terminus of Li is linked to the amino-terminus of Helix-2. In another embodiment, the arrangement from the amino- to the carboxyl-terminus is as follows: Helix-1, Li and Helix-2. A typical Helix 1-Linker-Helix 2 structure according to the present disclosure is depicted in FIGS. 1 and 3.

Preferably, the linker comprises a non-helical region. The first and last residues of the non-helical region can be any amino acid. Preferably, one or both residues are helix breaking or helix destabilizing residues, such as glycine or proline.

Such peptide linker include for example, but are not limited to, glycine linkers, serine linkers, mixed glycine/serine linkers, glycine- and serine-rich linkers, which are known to the skilled artisan.

In an embodiment of the present disclosure, the linker is absent.

In an embodiment of the present disclosure, the linker has a length of 1 to 50 amino acid residues. In another embodiment, the linker has a length of 1-30 amino acid residues. Yet in another embodiment, the linker has a length of 1-10 amino acid residues. In one embodiment, the linker has a length of 5 amino acids. In one embodiment, the linker comprises the amino acid sequence QGVDS (SEQ ID NO: 6). In one embodiment, the linker has the amino acid sequence QGVDS (SEQ ID NO: 6).

Variability of the Library

In general, a coiled-coil motif is tolerant to amino acid substitutions provided that the α-helix is not substantially destabilized.

The polypeptide library of the present disclosure is characterized by defined diversified positions at which mixtures of amino acid residues are placed. The diversified positions within the library is present on both α-helical peptides (Helix-1 and Helix-2) forming the HTH scaffold structure of the present disclosure.

In an embodiment, 6 positions in Helix-1 and 6 positions in Helix-2 are diversified.

Accordingly, the amino acid variations at the variable positions of the HTH scaffold of the present disclosure give rise to polypeptide members with different sequences.

The amino acid residues at variant positions are referred to as Var1, Var2, and Var3. This corresponds to heptad positions 'b', 'e', 'f' within the two α-helical peptides of the HTH scaffold.

The diversified amino acid residue positions are located on one face of the solvent exposed regions of the HTH scaffold, thereby forming the predominant binding site on the polypeptide members of the library.

As can be seen in FIGS. 2A and 2B, Var1 represents solvent-exposed amino acid residues which align on the same side of the HTH scaffold of the present disclosure and thus were used for diversification to generate the library of the present disclosure. See also Example 1.

In order to further increase the library size and to increase the contact interphase between the polypeptides of the library and their bound target molecules of interest, additional variable positions were introduced in Helix-1 and Helix-2. As denoted above, the amino acid residues at the additional variant positions of the present disclosure are referred to as Var2 and Var3, respectively.

The diversification employed in the library of the present disclosure may encompass both, naturally occurring and synthetic amino acid residues.

However, in certain embodiments, the diversified amino acid residue Var1, Var2 and Var3 are exclusively occupied by a mixture of the naturally occurring amino acids, as defined herein.

In a preferred embodiment of the present disclosure, said mixture is an equal mixture of the naturally occurring amino acids.

In yet a further embodiment, the diversified amino acid residue Var1 comprises a mixture of naturally occurring amino acids excluding G, P, C. G, P, C are known to break α-helical structures and thus were avoided. C was furthermore excluded in order to avoid the formation of potential di-sulfide bonds between two or more diversified amino acid residue positions. Furthermore, it was shown, that C residues appear significant less frequent in natural occurring α-helices compared to other natural occurring amino acid residue (Aurora et al., Protein Science (1998), 7:21-38) and Pace et al. (Biophysical Journal (1998), Vol. 75, 422-427)).

In an embodiment of the present disclosure, the diversified amino acid residue positions Var2 and Var3 comprise the naturally occurring amino acid residues E, D, K, R, N, Q, and H. In a preferred embodiment, said mixture is an equal mixture of said amino acid residues.

In one embodiment, Var2 comprises a mixture of the naturally occurring amino acid residues R, E, Q and Var3 comprises a mixture of the naturally occurring amino acid residues R, Q, H. In a preferred embodiment, said mixture is an equal mixture.

The library members of the present disclosure are characterized in that said polypeptides differ from each other in the defined set of 12 diversified amino acid residue positions.

Accordingly, the library members can differ from each other in at least one amino acid residue positions within the defined set of 12 diversified amino acid residue positions.

Alternatively, the library members can differ from each other in 1, 2, 3, 4, 5, 6, 7, 8, 9, 10, 11, or all 12, of these amino acid residue positions.

Accordingly, the library members can be distinguished from each other by the sequence difference(s) present in the defined set of the 12 diversified amino acid residue positions.

In certain embodiments, the polypeptide library of the present disclosure is displayed on bacteriophage. Phage display is known to have significant advantages in allowing the rapid selection of useful molecules. This method allows the preparation of libraries as large as $10^{10}$ unique peptide members, many orders of magnitude larger than libraries that may be prepared synthetically. Using such a robust platform allows for the display of large, diverse libraries.

In certain embodiments, a library of polypeptides according the present disclosure contains at least $10^2$, at least $10^3$, at least $10^4$, at least $10^5$, at least $10^6$, at least $10^7$, at least $10^8$, at least $10^9$ or even more different library members. In one embodiment, a library or collection of polypeptides of the present disclosure contains at least $10^6$ different library members.

In certain embodiments, the present disclosure provides a collection of nucleic acids encoding the library of polypeptides of the present disclosure.

In certain embodiments, the present disclosure provides a vector comprising the collection of nucleic acids encoding the library of polypeptides of the present disclosure.

In certain embodiments, the vector is a display vector. In other embodiments, the vector is an expression vector.

In certain embodiments, the present disclosure provides a recombinant host cell comprising the collection of nucleic acid molecules or the vector encoding the library of polypeptides of the present disclosure.

In certain embodiments, the present disclosure provides a method to isolate a polypeptide specific for an antigen, said method comprising the steps of:

a) contacting the library of the present disclosure with an antigen, b) removing those members of the library which do not bind to the antigen; and c) recovering those members of the library bound to the antigen In certain embodiments, the present disclosure provides a polypeptide identified using the library of polypeptides disclosed herein.

In an embodiment, the present disclosure provides a helix-turn-helix scaffold structure to an antibody or an antibody fragment, wherein said helix-turn-helix scaffold structure comprises a first and a second α-helical peptide that form an anti-parallel, coiled-coil structure.

In one aspect, the present disclosure provides a library of polypeptides, wherein each member of the library comprises a helix-turn-helix scaffold structure of the formula Helix-1-Li-Helix-2, wherein Helix-1 and Helix-2 comprise a first and second α-helical peptide, wherein each of said α-helical peptides comprises the amino acid sequence
X1-X2-Hy-Var1-X3-Hy-Var1-Var2-X4-Hy-Var1-X5-Hy-Var1-Var3 (SEQ ID NO: 1),
wherein
X1 is D, T, N, S or P,
X2 is E, P, Q, W or D,
X3 is M, A, I, Q or R,
X4 is A, L, R, M, K or E,
X5 is M, L, A, W, F or K, Hy is any amino-acid residue having a side chain exhibiting a hydrophobicity of greater than 0.62, and
Var1, Var2 and Var3 are mixtures of the natural occurring amino acids, excluding G, P, and C, Li is a linker, and said first and second α-helical peptide form an anti-parallel, coiled-coil structure.

In one embodiments of the present disclosure, additional amino acid residues at the amino terminus and/or the carboxyl-terminus of the helix-turn-helix scaffold are added.

Amino acid residues may also be replaced, deleted or added, for example to aid in the expression of library members in a preferred host species, to facilitate cloning of the molecule, to increase the stability of the peptide; to increase helix packing and so on. In one embodiment of the present disclosure, G is introduced at the amino- and carboxyl-terminus of the helix-turn-helix scaffold.

Methods for Generating Diversified Gene Libraries

Numerous methods for the generation of diversified genes and gene libraries are known. This includes the Slonomics technology (U.S. Ser. No. 12/414,174 and Van den Brulle et al., Biotechniques (2008), 45, 340-343)).

The Slonomics technology uses a defined number of standardized building blocks containing self-complementary regions. Two different classes of building blocks (called "splinkers" and "anchors") are used to successively build up tailor-made nucleotide libraries with any desired bias.

The diversified trinucleotide-containing oligonucleotide (TRIM) technology (WO93/21203) as well as oligonucleotide-mediated mutagenesis (Zoller et al. ((1987) Nucleic Acids. Res. 10 6487-6504)) are further methods for preparing diversified gene libraries.

Cassette mutagenesis is a further method for preparing the diversified gene libraries. The method is based on that described by Wells et al. ((1985) Gene 34:315).

Diversified gene libraries may be also prepared by standard solid phase peptide synthesis (Merrifield et al., J. Am. Chem. Soc., 1963, 85 (14), pp 2149-2154) with subsequent mixing of the purified products.

In certain embodiments, the synthesis of the polypeptide library of the present disclosure involves the step of producing a nucleic acid or vector library of at least 100 members, wherein each member encodes a polypeptide according to the present disclosure, and wherein the encoded different library members differ from each other in at least one out of a defined set of 12 diversified amino acid residue positions.

Upon expression in host cells, the polypeptide library of the present disclosure is obtained. These steps can be achieved in different ways, as will be known by the person skilled in the art. In general, such steps typically include transforming or transfecting a suitable host cell with a nucleic acid or vector library or an infectious particle which encodes the polypeptide library. Further, such steps typically include culturing said host cells under conditions suitable for the proliferation (multiplication, growth) of said host cells and a culturing step under conditions suitable for the production (expression, synthesis) of the encoded polypeptides. The culturing of host cells under conditions suitable for proliferation or expression is typically accomplished in the presence of media comprising components suitable for cell growth or induction of expression. In particular embodiments, the methods for the production of polypeptide libraries of the present disclosure further comprise the step of isolating the produced polypeptide from the host cells or medium. It is further noted that the expressed polypeptide libraries may, in addition to the different-sequence polypeptides, also contain multiple copies of identical polypeptides.

Phage-Display Methods

Phage display methods for proteins, peptides and mutated variants thereof, including constructing a family of variant replicable vectors containing a transcription regulatory element operably linked to a gene fusion encoding a fusion polypeptide, transforming suitable host cells, culturing the transformed cells to form phage particles which display the fusion polypeptide on the surface of the phage particle, contacting the recombinant phage particles with a target molecule so that at least a portion of the particle bind to the target, separating the particles which bind from those that do not bind, are known to the skilled artisan and may be used with the libraries disclosed herein.

In certain embodiments, the polypeptides of the present disclosure are linked to at least a portion of a phage coat protein to form a fusion protein containing the polypeptide disclosed herein. The fusion protein can be made by expressing a gene fusion encoding the fusion protein using known techniques of phage display. The fusion protein may form part of a phage or phagemid particle in which one or more copies of the peptide are displayed on the surface of the particle.

In certain embodiments, the present disclosure provides vectors comprising the fusion genes noted above, as well as a library of these vectors. The library of vectors may be in the form of a DNA library, a library of virus (phage or phagemid) particles containing the library of fusion genes or in the form of a library of host cells containing a library of the expression vectors or virus particles.

In certain embodiments, the present disclosure provides a method comprising the steps of preparing a library containing a plurality of vectors, each vector comprising a transcription regulatory element operably linked to a gene fusion encoding a fusion protein, wherein the gene fusion comprises a first gene encoding a peptide disclosed herein and a second gene encoding at least a portion of a phage coat protein, wherein the library comprises a plurality of genes encoding polypeptide fusion proteins.

The gene encoding the coat protein of the phage and the gene encoding the desired polypeptide portion of the fusion protein of the present disclosure (the polypeptide of the present disclosure linked to at least a portion of a phage coat protein) can be obtained by methods known in the art (see generally, Sambrook et al.) The DNA encoding the gene may be chemically synthesized (Merrfield (1963) 7 Am Chem Soc 85:2149).

The phage coat protein is preferably the gene III or gene VIII coat protein of a filamentous phage, such as, M13. Any suitable gene III vectors for display of peptides may be used, including fd-CATI (McCafferty et al. (1990) Nature (London) 348 552-554) and pHEN I (Hoogenboom et al. (1991) Nucleic Acids Res 19 4133-4137).

Suitable phage vectors, phagemid vectors and helper phage for use in accordance with the present disclosure are known to the skilled artisan.

Any suitable cells which can be transformed by electroporation may be used as host cells in the method of the present disclosure. Suitable host cells which can be transformed include gram negative bacterial cells such as *E. coli*. Suitable *E. coli* strains may include TG1F- or *E. coli* XL-I Blue (Stratagene).

In certain embodiments the host cell for electroporation is a competent *E. coli* strain containing a phage F' episome. Any F' episome which enables phage replication in the strain may be used.

After selection of the transformed cells, these cells are grown in culture and the vector DNA may then be isolated. Phage or phagemid vector DNA can be isolated and analysed using methods known in the art, for example, as described in Sambrook et al.

Panning Methods

Various panning methods may be used in accordance with the present disclosure. In a direct panning protocol the target is immobilized on a solid support. Examples of solid support are microtiter plates or tubes (e.g. Maxisorp plates, Maxisorp tubes, Nunc) or magnetic beads (Dynabeads, Invitrogen). The target can either be directly coated on plastic or beads (e.g. surface activated beads, such as Dynabeads), or via streptavidin when the target is biotinylated. Other tags can be used to capture the targets such as His-tags or, alternatively, an antibody directed against the target can also be used to capture the target on the support.

Also solution panning protocol may be used. Here, the target is captured on the solid support after incubation with the phage library. The target-phage interaction is performed in solution. To be able to wash away the non-binding phage, the target needs to be immobilized on a solid support.

In certain embodiments, an Fc-tagged target is used, whereby phages, which display a polypeptide of the present disclosure binding to the target, are captured with a Protein G or Protein A coated support (e.g. magnetic beads).

Polypeptides of the Present Disclosure

The polypeptides of the present disclosure can be synthesized by a variety of means, for example, by recombinant DNA technology or by chemical synthesis. Methods of peptide synthesis are known in the art.

Alternatively, the coding sequences for the polypeptides can be recombinant DNA molecules, which are introduced into expression vectors or phage by operatively linking the DNA to the necessary expression control regions (e.g. regulatory regions) required for gene expression.

The vectors can be introduced into the appropriate host cells such as prokaryotic (e.g., bacterial) or eukaryotic (e.g., yeast or mammalian) cells by methods well known in the art (see, e.g., "Current Protocol in Molecular Biology", Ausubel et al. (eds.), Greene Publishing Assoc. and John Wiley Interscience, New York, 1989 and 1992). Numerous cloning vectors are known to those of skill in the art, and the selection of an appropriate cloning vector is a matter of choice.

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence.

Depending on the expression system and host selected, the proteins of the present disclosure are produced by growing host cells transformed by an expression vector described above under conditions whereby the protein of interest is expressed.

The protein is then isolated from the host cells and purified. If the expression system secretes the protein into growth media, the protein can be purified directly from the media. If the protein is not secreted, it is isolated from cell lysates or recovered from the cell membrane fraction. The selection of the appropriate growth conditions and recovery methods are within the skill of the art.

The polypeptides of the present disclosure can then be purified by a number of techniques as known to the person skilled in the art.

It should be noted that the libraries and polypeptides of the disclosure are not naturally occurring proteins. Typically, the polypeptides of the present disclosure are recombinant, synthetic or semi-synthetic amino acid sequences, polypeptides or proteins.

As further described herein, the total number of amino acid residues in a polypeptide of the present disclosure can be in the range of 25 to 50000, in the range of 25-10000, in the range of 25 to 5000, in the range of 25-1000, in the range of 25-500, in the range of 25-250, in the range of 25-100, in the range of 25-50, or in the range of 25-35, depending mainly on the length of the flexible linkers interconnecting the two α-helical peptides and the additional moieties which may are linked to the helix-turn-helix scaffold.

The polypeptides of the present disclosure can be synthesized with additional amino acid residues added at their amino- and the carboxyl-terminus in order to allow linkage of the amino- and carboxyl terminal end of the polypeptides. The thus formed cyclized polypeptides may further increase the stability of the α-helical structure and improve resistance against proteolytic degradation by proteases.

The polypeptides of the present disclosure can be cyclized, introducing e.g. a disulfide bridge or a reduction insensitive thioether linkage. A disulfide bonde can be formed under oxidizing conditions between amino- and carboxyl-terminally introduced cysteine residues. A thioether bond according to the present disclosure may be formed for instance between N-chloroacetyl glycine present at the amino-terminus and a C residue present at the carboxyl-terminus.

In an embodiment of the present disclosure, the polypeptides according to the present disclosure are cyclic polypeptides.

In an embodiment of the present disclosure, the cyclic polypeptides are formed by a covalent bond.

In certain embodiments of the present disclosure, the covalent bond is a disulfide bond.

In certain embodiments of the present disclosure, the disulfide bond is formed by two C residues.

In certain embodiments of the present disclosure, the disulfide bond is formed between a C residue present at the amino-terminal end and a C residue present at the carboxyl-terminal end of the polypeptides of the present disclosure.

In certain embodiments of the present disclosure, the covalent bond is a thioether bond.

In certain embodiments of the present disclosure, the covalent bond is a thioether bond formed between N-chloroacetyl glycine and a C residue.

In certain embodiments, the covalent bond is a thioether bond formed between N-chloroacetyl glycine present at the amino-terminus and a C residues present at the carboxyl-terminus of the polypeptides of the present disclosure.

In certain embodiments, the covalent bond is a thioether bond formed between N-chloroacetyl glycine present at the amino-terminus and a C residues present at the carboxyl-terminus of the polypeptides of the present disclosure.

Polypeptide Fusion Proteins

The polypeptides provided by the library of the present disclosure may or may not be linked to one or more other moieties.

Such fusion-proteins may be prepared in any suitable manner, including genetically or chemically approaches.

Said linked moieties may contain secretory or leader sequences, sequences that aid detection, expression, separation or purification, or sequences that confer to increased protein stability, for example, during recombinant production.

Examples of potential moieties include beta-galactosidase, glutathione-S-transferase, luciferase, a T7 polymerase fragment, a secretion signal peptide, an antibody or antibody fragment thereof, a toxin, a reporter enzyme, a moiety being capable of binding a metal ion like a poly-histidine tag, a tag suitable for detection and/or purification, a homo- or hetero-association domain, a moiety which increases solubility of a protein, or a moiety which comprises an enzymatic cleavage site. Accordingly, a polypeptide of the disclosure may optionally contain one or more moieties for binding to other targets or target proteins of interest.

It should be clear that such further moieties may or may not provide further functionality to the polypeptides of the disclosure and may or may not modify the properties of the polypeptide of the disclosure.

The polypeptides of the present disclosure may be linked to one or more other moieties either directly by a single peptide bond or through one or more spacer(s) containing one or more ammo acid residues.

Suitable spacer(s) for use in linking the polypeptides of the disclosure with one or more moieties may be any spacer region used in the art to link peptides and/or proteins.

Some suitable spacers include for example, but are not limited to polypeptide spacers such as glycine spacers, serine spacers, mixed glycine/serine spacers, glycine- and serine-rich spacers, spacer composed of largely polar polypeptide fragments or spacers comprising an amino acid sequence forming a random coil conformation.

A spacer may be any suitable amino acid sequence having a length between 1 and 500 amino acid residues, such as between 1 and 100, between 1 and 50, between 1 and 10, or between 1 and 5 amino acid residues.

In an embodiment, the polypeptides of the present disclosure are linked to a poly-histidine tag. In other embodiment, the polypeptides of the present disclosure are linked to a FLAG tag. Yet in another embodiment, the polypeptides are linked to a FLAG and poly-histidine tag. In certain embodiments, said poly-histidine and/or FLAG tag is linked to the carboxyl- and/or amino-terminus of the polypeptide of the present disclosure.

In another embodiment, the polypeptides of the present disclosure are linked to a maltose binding protein (MBP). Maltose binding protein may increase the solubility during expression in bacterial hosts. In certain embodiments, the maltose binding protein domain is linked to the amino-terminus of the polypeptide.

In certain embodiments, the bacterial host used for expression is *Escherichia coli*.

In another embodiment, an enzymatic cleavage side is present between the carboxyl-terminus of the maltose binding domain and the amino-terminus of the polypeptides of the present disclosure. In certain embodiments, said enzymatic cleavage side is a FXa cleavage side.

In further embodiments, the polypeptides of the present are linked to an antibody or an antibody fragment thereof. In certain embodiments, said antibody fragment comprises a Fab fragment.

The antibody or antibody fragment thereof may have the same binding specificity or a different binding specificity as the polypeptides of the present disclosure.

The polypeptides of the present disclosure may be linked to the antibody or an antibody fragment thereof, either by a direct linkage to the amino- and/or carboxyl-terminus of the polypeptides or by a spacer region comprising one or more amino acid residues at the amino- and/or carboxyl-terminus of the polypeptides.

In certain embodiments, the polypeptides of the present disclosure are linked to the carboxyl-terminus of the heavy chain of an antibody. See FIG. 9A.

In other embodiments, the polypeptides of the present disclosure are linked to the carboxyl-terminus of the light chain of an antibody. See FIG. 9B.

In other embodiments, the polypeptides of the present disclosure are linked to the carboxyl-terminus of a heavy chain antibody Fab fragment. See FIG. 9C.

In other embodiments, the polypeptides of the present disclosure are linked to the carboxyl-terminus of an antibody Fc-fragment (CH2-CH3). See FIG. 9D.

In other embodiments, the polypeptides of the present disclosure are linked to the amino-terminus of an antibody Fc-fragment (CH2-CH3). See FIG. 9E.

In an embodiment, the present disclosure provides a helix-turn-helix scaffold structure linked to an antibody or an antibody fragment, wherein said helix-turn-helix scaffold structure comprises a first and a second α-helical peptide that form an anti-parallel, coiled-coil structure.

In an embodiment, the present disclosure provides a helix-turn-helix scaffold structure linked to the carboxyl-terminus of the heavy chains of an antibody, wherein said helix-turn-helix scaffold structure comprises a first and a second α-helical peptide that form an anti-parallel, coiled-coil structure.

In an embodiment, the present disclosure provides a helix-turn-helix scaffold structure linked to the carboxyl-terminus of the light chains of an antibody, wherein said helix-turn-helix scaffold structure comprises a first and a second α-helical peptide that form an anti-parallel, coiled-coil structure.

In an embodiment, the present disclosure provides a helix-turn-helix scaffold structure linked to the carboxyl-terminus of the heavy chain of an antibody Fab fragment, wherein said helix-turn-helix scaffold structure comprises a first and a second α-helical peptide that form an anti-parallel, coiled-coil structure.

In an embodiment, the present disclosure provides a helix-turn-helix scaffold structure linked to the amino-terminus of an antibody Fc fragment, wherein said helix-turn-helix scaffold structure comprises a first and a second α-helical peptide that form an anti-parallel, coiled-coil structure.

In an embodiment, the present disclosure provides a helix-turn-helix scaffold structure linked to the carboxyl-terminus of an antibody Fc fragment, wherein said helix-turn-helix scaffold structure comprises a first and a second α-helical peptide that form an anti-parallel, coiled-coil structure.

Functionality

The polypeptides of the present disclosure may be used for the prevention and treatment of diseases and disorders which are mediated by biological pathway(s) in which the target molecule of interest, against which the polypeptides are directed to, is involved.

The polypeptides of the present disclosure can be used to prevent or inhibit the interaction between one or more target molecules of interest and their corresponding receptors or natural binding partners, thereby preventing, inhibiting or reducing the signaling pathways that are mediated by those target molecules of interest and/or modulating the biological pathways and mechanisms in which those target molecules of interest are involved.

Methods for assaying for functional activity may utilize binding assays, such as the enzyme-linked immunosorbent assay (ELISA), radioimmunoassay (RIA), fluorescence activated cell sorting (FACS) and other methods that are well known in the art (see Hampton, R. et al. (1990; Serological Methods a Laboratory Manual, APS Press, St Paul, Minn.) and Maddox, D. E. et al. (1983; J. Exp. Med. 158:1211-1216). Alternatively, assays may test the ability of the peptide mimetic in eliciting a biological response as a result of binding to a biological target, either in vivo or in vitro. Such assays include B cell and T cell proliferation assays, and inhibition of proliferation assays (see Paul et al., (1991). Other suitable assays will be known to those of skill in the art.

Pharmaceutical Compositions

In certain embodiments, the present disclosure provides pharmaceutical compositions comprising one or more polypeptides obtainable by the methods of the present disclosure and optionally at least one pharmaceutically acceptable carrier together referred to herein as pharmaceutical compositions. The pharmaceutical compositions may further comprise at least one other pharmaceutically active compound.

The pharmaceutical compositions of the present disclosure can be used in the diagnosis, prevention and/or treatment of diseases and disorders associated with a target molecule of interest.

In particular, the present disclosure provides pharmaceutical compositions comprising polypeptides according to the present disclosure that are suitable for prophylactic, therapeutic and/or diagnostic use in a warm-blooded animal, and in particular in a mammal, and more in particular in a human being.

Generally, the polypeptides of the present disclosure may be formulated as a pharmaceutical preparation or compositions comprising at least one polypeptide according to the present disclosure and at least one pharmaceutically acceptable carrier, diluent or excipient and/or adjuvant, and optionally one or more further pharmaceutically active polypeptides and/or compounds. Such a formulation may be suitable for oral, parenteral, topical administration or for administration by inhalation.

In particular, the polypeptides of the present disclosure may be used in combination with other pharmaceutically active compounds that are or can be used for the prevention and/or treatment of the diseases and disorders in which a target molecule of interest is involved, as a result of which a synergistic effect may or may not be obtained. Examples of such compounds, as well as routes, methods and pharmaceutical formulations or compositions for administering them will be clear to the clinician.

In an embodiment, the present disclosure provides a pharmaceutical composition comprising one or more polypeptides of the present disclosure for use in the prevention and/or treatment of a disorder or condition associated with the undesired presence of a target molecule of interest specifically bound by the one or more polypeptides In an embodiment, the present disclosure provides a pharmaceutical composition comprising one or more polypeptides of the present disclosure for the use as a medicament.

In an embodiment, the disclosure provides a pharmaceutical composition comprising one or more polypeptides of the present disclosure for use in the prevention and/or treatment of autoimmune diseases, inflammatory diseases, cancer, neovascular diseases, infectious diseases, thrombosis, myocardial infarction, and/or diabetes.

In an further embodiment, the disclosure provides a method for the treatment of autoimmune diseases, inflammatory diseases, cancer, neovascular diseases, infectious diseases, thrombosis, myocardial infarction, and/or diabetes in a subject in need thereof using a pharmaceutical composition comprising one or more polypeptides of the present disclosure.

EXAMPLES

Example 1: Design of the Library

The design of the library is based on a combined approach taking into account statistical, structural and rational factors.

This includes the analysis of the most abundant amino acid residues found in natural α-helical structures. Such amino acids may have favorable biophysical properties that would lead to more efficient development and increase the safety and efficacy of the resulting polypeptides in patients. The abundancy of natural occurring amino acids in α-helices was obtained from literature, such as Aurora et al. (Protein Science (1998), 7:21-38) and Pace et al. (Biophysical Journal (1998), Vol. 75, 422-427). These data were used to catalog residue preferences at the amino- and carboxyl-terminal ends of α-helices, as well as to catalog residue preferences found more in the central region of α-helices. A particular focus was on those amino acids that occur at positions that are relevant for the formation of the α-helical coiled-coil structure in aqueous solution.

Data was subsequently transferred into a template to design potential α-helical reference sequences. Such a reference sequence has a length of 15 amino acid residues and comprises two consecutive heptad sequences. For each of said 15 amino acid residue positions, the five to six most frequently occurring amino acid residues were considered as a basis for designing two independent α-helical peptide sequences being able to from a stabilized anti-parallel orientated coiled-coil structure in aqueous solution.

In order to select the optimal reference sequence for the generation of a polypeptide library according of the present disclosure, additional structural consideration for promoting helix formation and stabilizing the α-helical coiled-coil structure were taken into account to select the most appropriate amino acid residue at each position.

Accordingly, a reference polypeptide sequence (HTHdes2) comprising two α-helical peptides and a linker segment as depicted in FIG. 3, was designed and selected for synthesis and testing for α-helical content by circular dichroism (CD) spectra measurements. The obtained data confirmed that the HTHdes2 reference sequence resulted in a high degree of α-helical structure and a low content of random coiled structures in solution. Additional studies revealed that the HTHdes2 sequence was extremely resistant towards thermal and chemical denaturation. See also Example 12.

In addition, an in silico T cell epitope screening for the HTHdes2 reference sequence (Lonza, The Epibase™ In Silico tool) revealed a low to no immunogenicity risk for the generated construct.

The HTHdes2 reference sequence was subsequently used for the construction of the polypeptide library according to the present disclosure.

In a first step, the inventors had to decide which specific amino acid positions on the HTHdes2 reference sequence should to be used for diversification without destabilizing the α-helical secondary structure of the two HTH forming peptides and without compromising the formation of the coiled-coil structure.

Stabilizing a HTH structure may be achieved by diversifying only one of the two alpha helical peptides as it has been described by Fujii et al (Biochemistry, 47, 6745-6751 (2008)). In this scenario, the second non-diversified peptide retains its α-helical structure and stabilizes the helix-turn-helix structure. However, diversification of only one peptide significantly limits the achievable library size and narrows down the interaction interphase between the polypeptides of the library and their bound target molecules of interest.

Thus, the inventors decided to diversify both α-helical peptides. The variable positions present on both α-helical peptides contribute to an enlarged interaction interphase between a particular polypeptide and its target antigen, thus resulting in improved specificity and affinity.

As described herein and as shown in FIGS. 1 and 3, the amino acid positions, which were primarily selected for diversification, were heptad positions 'b' and 'e' of Helix-1 and Helix-2. Since each helix comprises two heptads, 4 amino acid position are diversified per helix. These amino acid positions, herein referred to as Var1 are displayed in the same relative parallel orientation and are the key solvent exposed residues for interacting with a target antigen of interest (FIGS. 2A and 2B). Because of this predominant role, the respective positions were fully diversified with 17 naturally occurring amino acids, leaving out only G, P and C which are known to break α-helical structures.

The assembly of the two α-helical peptides provides for a total of eight diversified amino acid residues, all of which are displayed in the same relative parallel orientation out of the HTH scaffold structure with a slight spatial off-set of the diversified positions within the two aligned peptides. Consequently, a wide and flat interaction interface is formed over the whole length of the HTH scaffold structure, which allows an optimal protein-protein interaction with a target antigen of interest.

In order to further increase the library size and the interaction interface, additional amino acid residues within the HTHdes2 reference sequence were considered for diversification. Amino acid residues present at heptad positions f are also orientated towards the interaction interface even though not completely in a parallel fashion. Based on the local geometry, the orientation of residues at heptad positions f appear slightly angulated (FIG. 1 and FIGS. 2A and 2B) but the residues may still be able to interact with a target antigen. Thus, 4 of said heptad f positions were selected for further diversification and were named Var2 and Var3.

Based on the angulated orientation of the residues towards the interaction interface, amino acids with charged or polar side chains like E, D, K, R, N, Q, and H were considered as the optimal residues for diversification of Var2 and Var3. In this scenario, the terminally located polar or charged functional groups of each residue is capable of interacting with the surrounding solvent whereas the nonpolar carbon backbone can interact with the target antigen. Final selection of the 3 amino acid residues used for diversification of Var2 and Var3 was driven by their natural occurrence in α-helices at corresponding positions as described by Aurora et al. (Protein Science (1998), 7:21-38) and Pace et al. (Biophysical Journal (1998), Vol. 75, 422-427). Therefore, a slightly different amino acid residue mixture was used for Var2 and Var3. The theoretical library size therefore amounts to 5, $6 \times 10^{11}$ library members.

In summary, the library of the present disclosure was built to maximize the number of diversified positions without compromising the stabilizing α-helical structures which form the HTH scaffold structure of the present disclosure.

Example 2: Generation of the HTH-lib1 Library

The DNA fragments containing the polypeptide library sequence were synthesized as follows: The flanking constant regions comprising a signal sequence, epitope tag and spacer regions were synthesized by gene synthesis. The polypeptide library encoding the polypeptide sequence with 12 diversified amino acid positions was synthesized with the Slonomics technology. The resulting 279 bp synthetic linear DNA fragments comprising the polypeptide library and the flanking constant regions were cloned into the pPEPdisC3fl_HTH-lib1 display vector (as described in WO2015166036 with minor modifications).

Example 3: Determination of Display Rate

Display of polypeptides on the produced phage was evaluated by Western Blot. After SDS-PAGE separation, proteins were detected using an antibody against the FLAG epitope (M2, Sigma-Aldrich) as this epitope tag is encoded by the pIII (fl)-polypeptide library and therefore part of the displayed peptides. For detection of total pIII, an anti-pIII antibody (MiBiTec) was used. Helper phages displayed approx. 2-3 library peptides per phage and on hyper phages all 5 pIII copies carry the library peptides.

Furthermore, display of polypeptides on the produced phage was qualitatively evaluated by ELISA, utilizing an anti-M13 antibody (GE Healthcare) for phage capturing and two antibodies for specific detection. A monoclonal anti-M13 conjugated to HRP (Amersham) and a monoclonal antibody against the FLAG epitope conjugated to AP (Sigma).

The results confirmed a high display rate of library polypeptides.

Example 4: Quality Control

Another important aspect is the evaluation of the quality and functionality of the polypeptide HTH-lib1 library. A qualitative assessment of the phage library, with respect to amino acid distribution, frequency and redundancy was carried out using Sanger sequencing.

175 clones were analyzed from the library design shown in FIG. 3 using Sanger sequencing. Sequencing results are shown in FIG. 4A. FIG. 4A shows the position and distribution of the indicated amino acids at diversified positions in Helix-1 and Helix-2, respectively.

Of the 175 individual clones sampled, a well-balanced distribution of the natural occurring amino acids except G, P and C was identified for Var1. Similarly, a well-balanced distribution of the amino acids R, Q and E for Var2 and of amino acids R, Q and H for Var3 could be confirmed.

FIG. 4B shows the expected amino acid distribution in comparison to the sequencing results (given in percentage). These results demonstrate that the composition of the synthesized library is essentially identical to the library design.

Example 5: Pannings and Screenings

The suitability of the polypeptide library HTH-lib1 disclosed herein for the identification of potential therapeutic peptides was analyzed using available model antigens.

The HTH-lib1 library was used for test selections against model Target-X. Target-X was used as a hIgFc fusion protein. Selections were performed in solution using Protein G coupled magnetic beads (Dynabeads Protein G, Life Technologies) which are able to capture the antigen-phage complex by the human Fc-tag of the antigen.

The polypeptide library was handled according to published standard protocols for phage display based peptide selections (Zwick, M. B., Menendez, A., Bonnycastle, L. L. C. and Scott, J. K. (2001). In C. F. Barbas, D. R. Burton, J. K. Scott and G. J. Silverman, (Eds.), *Phage Display: A Laboratory Manual* (pp. 18.1-18.44). New York: Cold Spring Harbor Laboratory Press) with minor adjustments in terms of selection stringency and adaptation to phagemide vector system.

The test selections were performed over 3 subsequent enrichment rounds with monitoring of specific sequences by conventional sequencing. In short, all pannings were completed with various antigen concentrations (100 nM for round 1, 50 nM for round 2, and 25 nM for round 3) under standard washing conditions. The target protein was incubated with pre-adsorbed phages. Washing of the coated magnetic Dynabeads was carried out with a magnetic particle separator and incubations were done by overhead rotation in low binding tubes. Subsequently, the specifically bound phages were eluted using Glycine/HCl.

*E. coli* TG1F' with an OD600 nm of 0.6-0.8 was added to the phage eluates of each selection and was incubated in an incubator without shaking. After infection bacteria were plated out evenly on two large LB/Chloramphenicol/Glucose agar plates for each selection and incubated overnight at 37° C. and Glycerol phage stocks were prepared.

For the following panning rounds bacterial suspensions of each pool were collected and used to propagate phages for an additional panning round as described above.

After each round of panning the phage titer was determined. The expected range goes from 1.0E+10-1.0E+12 phage/ml for the input and 1.0E+07-1.0E+09 phage/ml for the output. Table 3 shows the output after each round of panning and all values are in the expected range.

TABLE 3

| | | Phage output titers | | | |
|---|---|---|---|---|---|
| Library | Panning Strategy | Target | Phage Output 1st round | Phage Output 2nd round | Phage Output 3rd round |
| HTH-lib1 | Solution | Target-X/hFc | 1.11E+07 | 1.45E+07 | 4.06E+08 |

After completion of the panning rounds phage output pools were subcloned via PCR into an expression vector to facilitate the cytoplasmic expression of the polypeptides in *E. coli*. Expression of single clones resulted in the production of polypeptides that were N-terminally linked to the Maltose Binding Protein (MBP) and that include a protease cleavage site.

To check for target specificity, an ELISA screen was carried out by capturing the Fc-tagged cynomolgus and human Target-X protein as well as an unrelated Fc-tagged protein on the surface of a microtiter plate pre-coated with an anti-human Fc specific antibody (Jackson Immuno Research) and *E. coli* lysates containing the polypeptides obtained from the panning outputs. Bound polypeptides were detected by the encoded FLAG tag using anti-FLAG detection (anti-FLAG-AP, Sigma Aldrich). To analyze MBP-polypeptide fusion expression, anti-His capture (R&D Systems) and anti-MBP detection (Abcam) was applied.

In total, 280 polypeptides were identified recognizing the cynomolgus Target-X/Fc fusion protein in ELISA. Furthermore, almost all cynomolgus positive clones (98%) revealed cross-reactivity to the human Target-X protein but no binding to an irrelevant Fc-fusion protein.

Sequence analysis and ELISA of panning outputs from subsequent panning rounds revealed an enrichment of specific binders, i.e. binders that bind to the target protein but not to unrelated proteins.

Example 6: Sequencing Results of Target-X Specific Polypeptides

Figure 9:
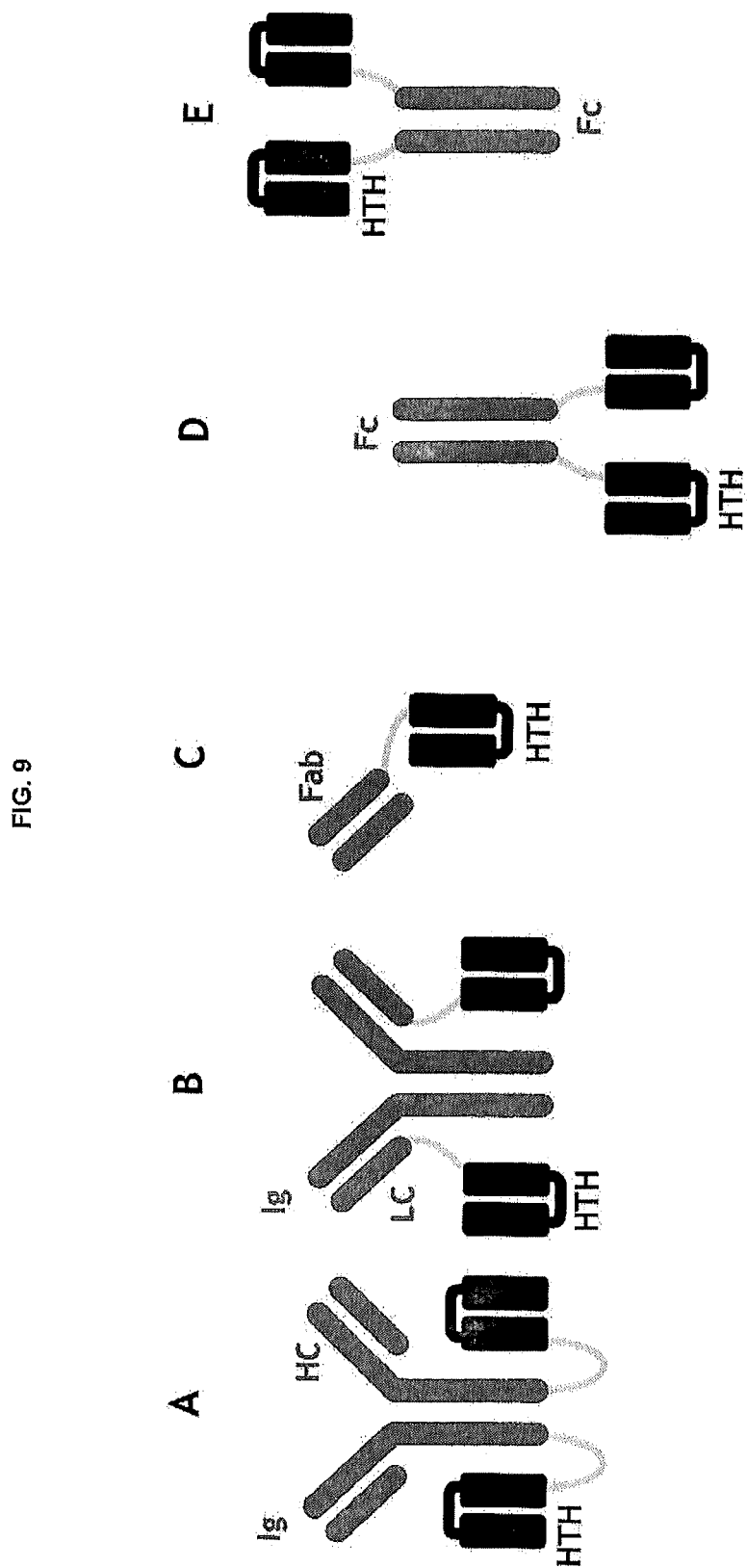
FIG. 9, views A, B, C, D and E, show illustrations of HTH scaffolds as disclosed herein, linked to antibodies or antibody fragments. View A of FIG. 9 depicts two HTH scaffolds linked to the carboxyl-terminus of the heavy chains of an antibody. View B of FIG. 9 depicts two HTH scaffolds linked to the carboxyl-terminus of the light chains of an antibody. View C of FIG. 9 depicts a HTH scaffold linked to the carboxyl-terminus of the heavy chain of an antibody Fab-fragment. View D and view E of FIG. 9 depicts an HTH scaffold linked to the carboxyl- or amino-terminus of an Fc-fragment of an antibody.

Sanger sequencing was performed to analyze the binders that are specific for the human and the cynomolgus Target-X/Fc fusion protein (see Example 5). The sequencing results revealed a diverse number of target specific polypeptides as depicted in FIG. 9. This demonstrates that the library of the present disclosure can be used to identify a large variety of polypeptides that are specific for the target protein of interest.

As a next step, selected polypeptides from the screening campaign were produced in larger scale in order to characterize them in more detail for properties, such as ELISA and cell binding, affinity, and functional activity in a relevant in vitro assay.

Example 7: Characterization of Purified Target-X Specific Polypeptides for ELISA Binding Binding to Human and Cynomolgus Target-X was Tested in an ELISA.
Methods:
1.5 µg/ml of each Fc fusion protein was captured via an anti-human-Fc-capture (Jackson Immuno Research) specific antibody on Maxisorp plates and bound MBP-polypeptide fusions were detected using an anti-FLAG detection antibody.
Results:
All 18 polypeptides showed significant and specific binding to both, recombinant cynomolgus and human Target-X/Fc proteins. $EC_{50}$ values range from the single to triple digit nanomolar range.

TABLE 4

ELISA binding to different Target-X species.

| | ELISA/$EC_{50}$ (nM) | |
|---|---|---|
| | cyno | human |
| HTH00024 | 12.6 | 478 |
| HTH00025 | 633 | 459 |
| HTH00029 | 96 | 98 |
| HTH00031 | 80 | 86 |
| HTH00032 | 203 | 337 |
| HTH00033 | 738 | 678 |
| HTH00034 | 3.1 | 3.1 |
| HTH00035 | 28 | 20 |
| HTH00036 | 85 | 79 |
| HTH00037 | 65 | 109 |
| HTH00039 | 54 | 80 |
| HTH00040 | 90 | 150 |
| HTH00041 | 111 | 114 |
| HTH00042 | 19.4 | 15.7 |
| HTH00043 | 154 | 194 |
| HTH00044 | 485 | 429 |
| HTH00055 | 93 | 94 |
| HTH00056 | 196 | 503 |

These results confirms the highly specific nature of the polypeptides isolated from the library of the present disclosure.

Example 8: Characterization of Target-X Specific Polypeptides for Cell Binding (FACS)

Cell Binding to Cynomolgus Target-X Expressed on CHO Cells was Analyzed by FACS.
Methods:
CHO cells stable transfected with cynomolgus Target-X were adjusted to $2\times10^6$ cells/ml in PBS/3% FCS/0.02% $NaN_3$ (FACS buffer). FACS staining was performed in V-bottom 96-well microtiter and $1\times10^5$ cells per well were mixed with purified polypeptides, diluted in FACS buffer and incubated on ice for 1 h. Cells were then washed 4× with 150 µl FACS buffer/well and taken up in 50 µl rabbit anti-MBP (Abcam), diluted 1:10000 in FACS buffer. After 1 h incubation on ice cells were washed 4× with FACS buffer and taken up in 50 µl phycoerythrin-conjugated anti-rabbit secondary antibody (Jackson Immuno Research), diluted 1:100 in FACS buffer. After 30 min incubation on ice, cells were washed 4× with FACS buffer, resuspended in 100 µl FACS buffer and cell surface binding of cynomolgus Target-X specific antibodies was measured via FL2 fluorescence intensity of cells in FACSArray (Becton Dickinson).
Results:
19 purified polypeptides showed specific cell binding to cynomolgus Target-X expressed on CHO cells with $EC_{50}$ values ranging from the single to triple digit nanomolar range.

TABLE 5

Cell binding (FACS) to cynomolgus Target-X-CHO cells.

| | Cell Binding/$EC_{50}$ (nM) |
|---|---|
| HTH00024 | 17.5 |
| HTH00025 | 253 |
| HTH00027 | 235 |
| HTH00029 | 333 |
| HTH00031 | 146 |
| HTH00032 | 26 |
| HTH00033 | 412 |
| HTH00034 | 4.9 |
| HTH00035 | 688 |
| HTH00036 | 144 |
| HTH00037 | 247 |
| HTH00039 | 93 |
| HTH00040 | 14.6 |
| HTH00041 | 32 |
| HTH00042 | 82 |
| HTH00043 | 159 |
| HTH00044 | 140 |
| HTH00055 | 580 |
| HTH00056 | 53 |

Again, this result confirms the highly specific nature of the polypeptides isolated from the library of the present disclosure. Polypeptides are also able to bind to the target protein on whole cells.

Example 9: Affinity Determination of a Target-X Specific Polypeptide Using Surface Plasmon Resonance Kinetic characterization of the interaction between cynomolgus Target-X/Fc and the Target-X-specific polypeptide was carried out in ligand-capture format, with the polypeptide being applied as analyte in solution.

Methods:

A Biacore CM5 sensor chip (GE Healthcare) was covalently modified to generate a high-density capture surface specific for human Fc. All flowcells were immobilized with approx. 3500 RU MabSelect SuRe™ Ligand (GE Healthcare; 50 µg/mL in 10 mM Acetate buffer pH 4.5) using standard EDC-NHS amine coupling chemistry. 10 mM HBS-EP+ pH7.4 (GE Healthcare) was used as running buffer and sample diluent. During kinetic characterization, Target-X/Fc was captured onto an anti-human-Fc specific flowcell (20 nM; 75 s injection; capture level approx. 250 RU), followed by analyte injection (association) for 180 s and dissociation (variable times; up to 600 s; flow rate 40 µL/min). A 2-fold serial dilution series of analyte concentrations from 1.37 to 1000 nM was analyzed. At the end of each cycle, captured ligand and bound analyte were removed with 10 mM Glycine/HCl pH 1.5 by 2 injections a 30 s. Blank injections (analyte concentration=0 nM) were included, and subtracted for double referencing. The resulting sensorgrams were evaluated with Biacore T200 Evaluation Software 3.0 (GE Healthcare) using 1:1 kinetic and steady state models.

Results:

The affinity of the Target-X specific polypeptide was measured on captured cynomolgus Target-X/Fc in a Biacore system. The affinity of the polypeptide was 36 nM in a kinetic model and 45 nM in a steady state model (Table 6).

This demonstrates that the polypeptides of the present disclosure are not just highly specific but also bind with a high affinity to their targets.

Example 10: Cynomolgus Target-X/Receptor Binding Inhibition Assay (ELISA)

Methods:

10 µg/ml of the Target-X related recombinant receptor protein was coated on a MSD-plate and blocked with milk powder. Different concentrations of a Target-X specific MBP-free polypeptide were mixed with 0.5 µg/ml cynomolgus Target-X/Fc and incubated for 30 min at RT. After washing the blocked MSD-plate, the polypeptide-Target-X/Fc mixtures were applied to the plate and incubated for 1 h at RT. After washing, receptor bound Target-X was detected using an ECL-conjugated anti-human Fc specific antibody (1:2000, Jackson Immuno Research). Inhibition of the specific receptor/target interaction by the polypeptide lead to decreasing signals for Target-X/Fc bound to its receptor.

Results:

A purified cynomolgus Target-X specific MBP-free polypeptide was analyzed for its potential inhibitory in vitro activity on receptor/cynomolgus Target-X interaction. The polypeptide showed significant receptor/cynomolgus Target-X interaction inhibition in an ELISA with an $IC_{50}$ value of 14.7 nM.

TABLE 6

Summary of the results from the in vitro characterization

| | MBP-free peptide: |
|---|---|
| ELISA (EC50) | 6.3 nM |
| FACS (EC50) | 6.5 nM |
| SPR (Kd) | 45 nM |
| Inhibition (IC50) | 14.7 nM |

Example 11: Structural Analysis of the Helix-Turn-Helix Design of Target-X Specific Polypeptides α-helical content of a Target-X specific polypeptide was analyzed by measuring circular dichroism (CD) spectra in 10 mM phosphate buffer (pH 7.2) with a peptide concentration of 0.1 mg/ml, using a Chirascan Plus CD-Spectrophotometer (Applied Photophysics).

Figure 8:
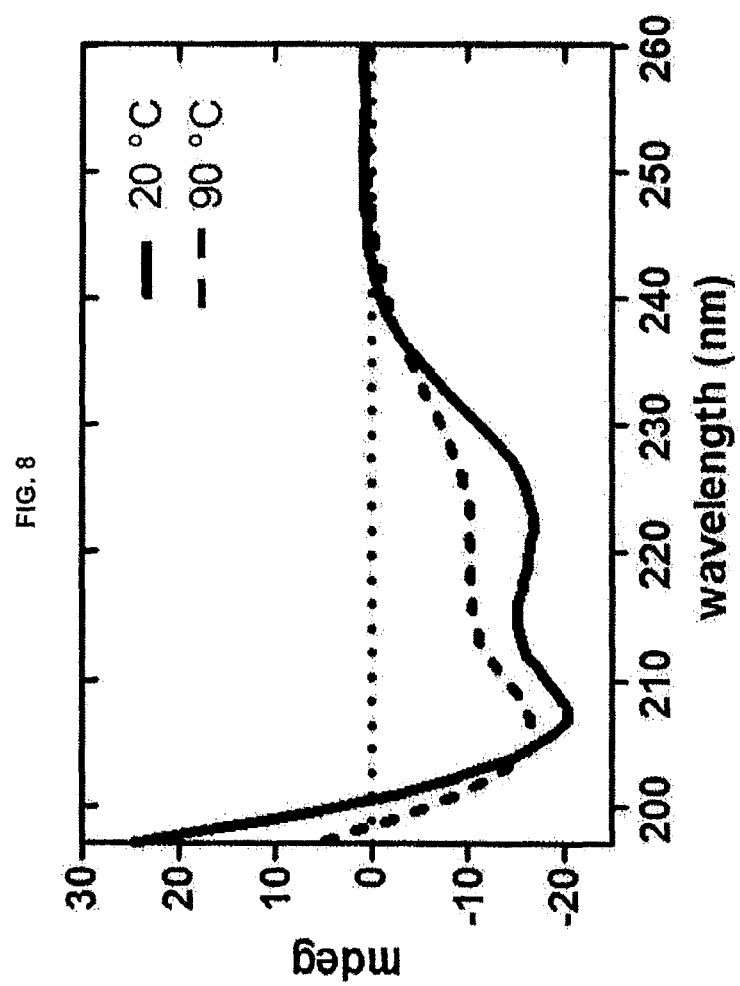
FIG. 8 shows two circular dichroism (CD) spectra of a Target-X specific polypeptide in 10 mM phosphate buffer at pH 7.2 at 20° C. and a polypeptide concentration of 0.1 mg/ml treated at temperatures of 20° C. and 90° C.

As shown in FIG. 8, the polypeptide exhibited double minima at 208 and 222 nm, indicating that the polypeptide has high content of α-helical structure in aqueous solution.

In addition, the thermal stability was determined by incubating the polypeptide in aqueous solution at increasing temperatures ranging from 20° C. to 90° C. Analysis of the CD spectra revealed that the polypeptide showed almost no structural unfolding even after treatment at 90° C. (FIG. 8).

Example 12: Stability of the Helix-Turn-Helix Design

Stability against chemical denaturation was determined by incubating a polypeptide comprising the HTHdes2 reference sequence, in 2 and 4 molar Guanidin-Hydrochlorid (GdmHCL) at 20° C. Even treatment with 4M GdmHCL did not resulted in complete unfolding of the polypeptide. In a further experiment, the polypeptide was treated with 2M GdmHCL plus increasing temperatures ranging from 22° C. to 90° C. Again, even after treatment with 2M GdmHCL at 90° C., no complete unfolding of the polypeptide could be observed.

Stability against low pH denaturation was examined for a sequence variant of the HTHdes2 reference sequence polypeptide, wherein 6 amino acid residues in Helix-2 were exchanged. Treatment of the polypeptide in pH 2 for 60 min. with or without subsequent neutralization to a pH 7.2 did not altered the α-helical content of the polypeptide.

All the performed studies clearly demonstrate the superior stability properties of the polypeptides, which can be isolated from the library of the present disclosure.

The invention claimed is:

1. A pharmaceutical composition comprising a polypeptide isolated from a library of polypeptides, wherein each member of the library comprises a helix-turn-helix scaffold structure of the formula Helix-1-Li-Helix-2, wherein Helix-1 and Helix-2 comprise a first and second α-helical peptide, wherein each of said α-helical peptides comprises the amino acid sequence (SEQ ID NO: 1)
X1-X2-Hy-Var1-X3-Hy-Var1-Var2-X4-Hy-Var1-X5-Hy- Var1-Var3, wherein X1 is D, T, N or S, X2 is E, P, Q, W or D, X3 is M, A, I, Q or R, X4 is A, L, R, M, K or E, X5 is M, L, A, W, F or K, Hy is any amino-acid residue having a side chain exhibiting a hydrophobicity of greater than 0.62, and Var1, Var2 and Var3 are each diversified amino acid residues selected from mixtures of the natural occurring amino acids, excluding G, P and C, Li is a linker, and said first and said second α-helical peptide form an anti-parallel, coiled-coil structure.

2. The pharmaceutical composition of claim 1 wherein the linker Li comprises 1 to 30 amino acid residues (SEQ ID NO: 2).

3. The pharmaceutical composition of claim 1, wherein

X1 is D,

X2 is E,

X3 is Q in Helix-1 and A in Helix-2,

X4 is E in Helix-1 and K in Helix-2, and

X5 is K in Helix-1 and M in Helix-2 as depicted in SEQ ID NO:3.

4. The pharmaceutical composition of claim 1, wherein Hy is L, V or I as depicted in SEQ ID NO:4.

5. The pharmaceutical composition of claim 1, wherein

Var2 is a mixture of R, Q and E, and

Var3 is a mixture of R, Q and H as depicted in SEQ ID NO:5.

6. The pharmaceutical composition of claim 1, wherein polypeptide is linked to at least one additional moiety.

7. The pharmaceutical composition of claim 6, wherein said additional moiety is an antibody or antibody fragment thereof, a toxin, a cytokine, a reporter enzyme, a moiety being capable of binding a metal ion, a tag suitable for detection and/or purification, a homo- or hetero-association domain, a moiety which increases solubility of a protein, or a moiety which comprises an enzymatic cleavage site.

8. The pharmaceutical composition of claim 1 further comprising at least one pharmaceutically acceptable carrier.

9. A pharmaceutical composition comprising a helix-turn-helix scaffold structure of formula Helix-1-Li-Helix-2, linked to an antibody or an antibody fragment, wherein said helix-turn-helix scaffold structure comprises a first and a second α-helical peptide that form an anti-parallel, coiled-coil structure, wherein each of said α-helical peptides comprises the amino acid sequence (SEQ ID NO: 1)
X1-X2-Hy-Var1-X3-Hy-Var1-Var2-X4-Hy-Var1-X5-Hy- Var1-Var3, wherein X1 is D, T, N, S or P, X2 is E, P, Q, W or D, X3 is M, A, I, Q or R, X4 is A, L, R, M, K or E, X5 is M, L, A, W, F or K, Hy is any amino-acid residue having a side chain exhibiting a hydrophobicity of greater than 0.62, Var1, Var2 and Var3 are mixtures of the natural occurring amino acids, excluding G, P and C, and Li is a linker.

10. The pharmaceutical composition of claim 9 further comprising at least one pharmaceutically acceptable carrier.

11. A method for preventing or treating a disorder or condition associated with the undesired presence of a target molecule of interest specifically bound by the polypeptide of the pharmaceutical composition of claim 1 in a subject, said method comprising administering to the subject the pharmaceutical composition of claim 1.

12. The method of claim 11 wherein the disorder or condition associated with the undesired presence of a target molecule of interest is an autoimmune disease, inflammatory disease, cancer, neovascular disease, infectious disease, thrombosis, myocardial infarction or diabetes.

13. A method for preventing or treating a disorder or condition associated with the undesired presence of a target molecule of interest specifically bound by the polypeptide of the pharmaceutical composition of claim 9 in a subject, said method comprising administering to the subject a pharmaceutical composition comprising a helix-turn-helix scaffold structure of formula Helix-1-Li-Helix-2, linked to an antibody or an antibody fragment, wherein said helix-turn-helix scaffold structure comprises a first and a second α-helical peptide that form an anti-parallel, coiled-coil structure, wherein each of said α-helical peptides comprises the amino acid sequence

```
                                    (SEQ ID NO: 1)
X1-X2-Hy-Var1-X3-Hy-Var1-Var2-X4-Hy-Var1-X5-Hy-

Var1-Var3,
``` wherein
X1 is D, T, N, S or P,
X2 is E, P, Q, W or D,
X3 is M, A, I, Q or R,
X4 is A, L, R, M, K or E,
X5 is M, L, A, W, F or K,
Hy is any amino-acid residue having a side chain exhibiting a hydrophobicity of greater than 0.62,
Var1, Var2 and Var3 are each diversified amino acid residues selected from mixtures of the natural occurring amino acids, excluding G, P and C, and
Li is a linker; and
wherein the disorder or condition associated with the undesired presence of a target molecule of interest is an autoimmune disease, inflammatory disease, cancer, neovascular disease, infectious disease, thrombosis, myocardial infarction or diabetes.

* * * * *